US012570742B2

(12) United States Patent
Li

(10) Patent No.: US 12,570,742 B2
(45) Date of Patent: Mar. 10, 2026

(54) ANTI-SIRPα MONOCLONAL ANTIBODIES AND USES THEREOF

(71) Applicant: LaNova Medicines Limited Company, Shanghai (CN)

(72) Inventor: RunSheng Li, Shanghai (CN)

(73) Assignee: LaNova Medicines Limited Company, Shanghai (CN)

( * ) Notice: Subject to any disclaimer, the term of this patent is extended or adjusted under 35 U.S.C. 154(b) by 906 days.

(21) Appl. No.: 17/530,302

(22) Filed: Nov. 18, 2021

(65) Prior Publication Data

US 2022/0169726 A1 Jun. 2, 2022

Related U.S. Application Data

(63) Continuation of application No. PCT/CN2020/138800, filed on Dec. 24, 2020.

(30) Foreign Application Priority Data

Dec. 24, 2019 (WO) ................ PCT/CN2019/127915

(51) Int. Cl.
*C07K 16/28* (2006.01)
*A61K 39/00* (2006.01)

(52) U.S. Cl.
CPC .......... *C07K 16/2803* (2013.01); *A61K 39/00* (2013.01); *C07K 16/28* (2013.01); *C07K 16/2896* (2013.01); *A61K 2039/507* (2013.01); *C07K 2317/565* (2013.01); *C07K 2317/567* (2013.01); *C07K 2317/622* (2013.01)

(58) Field of Classification Search
None
See application file for complete search history.

(56) References Cited

U.S. PATENT DOCUMENTS

2019/0119396 A1 4/2019 Liu

FOREIGN PATENT DOCUMENTS

| CN | 106456749 A | 2/2017 | |
|----|----|----|----|
| CN | 109862910 A | 6/2019 | |
| WO | WO-2015138600 A2 * | 9/2015 | ......... A61K 51/1027 |
| WO | 2018026600 A1 | 2/2018 | |
| WO | 2018057669 A1 | 3/2018 | |
| WO | 2018107058 A1 | 6/2018 | |
| WO | 2018190719 A2 | 10/2018 | |
| WO | 2018210793 A3 | 11/2018 | |
| WO | 2018210795 A1 | 11/2018 | |

(Continued)

OTHER PUBLICATIONS

Weiskopf, et. al, Science, 2013, 341, 88-91 (Year: 2013).*

(Continued)

*Primary Examiner* — Michael Szperka
*Assistant Examiner* — Samantha Lake Hopkins
(74) *Attorney, Agent, or Firm* — Sheppard, Mullin, Richter & Hampton LLP

(57) ABSTRACT

Provided are antibodies or fragments thereof having binding specificity to both variant 1 and variant 2 of the signal regulatory protein alpha (SIRPα) protein. The antibodies and fragments can dose-dependently and efficiently block the interaction between SIRPα and CD47, and effectively induce macrophage-mediated phagocytosis of tumor cells expressing CD47.

13 Claims, 5 Drawing Sheets

Specification includes a Sequence Listing.

248G3F6 IC₅₀ = 355.8 ng/ml
300A6A6 IC₅₀ = 383.1 ng/ml

(56) References Cited

FOREIGN PATENT DOCUMENTS

WO          2019226973  A1      11/2019

OTHER PUBLICATIONS

Yanagita, et. al, JCI Insight, 2017, 2, 1-15 (Year: 2017).*
International Search Report and Written Opinion for PCT/CN2020/
138800 dated Mar. 31, 2021, 13 pages.
Voets et al., "Functional characterization of the selective pan-allele
anti-SIRP[alpha] antibody ADU-1805 that blocks the SIRP[alpha]-
CD47 innate immune checkpoint", Journal for Immunotherapy of
Cancer, vol. 7, No. 1, Dec. 1, 2019, 16 pages, Pub Dec. 4, 2019.
Gabriela et al., "Novel SIRP Antibodies with Differentiated Char-
acteristics for Targeting Innate Immunity in Cancer", Nov. 6, 2019.
Retrieved from the Internet: URL:https://archoncology.com/wp-
content/uploads/2019/11/Arch_Oncology_SITC_2019_Novel_SIRP-_
Poster.pdf, 3 pages.
Gabriela et al., "Novel SIRP antibodies with differentiated charac-
teristics for targeting innate immunity in cancer", Journal for
Immunotherapy of Cancer, vol. 7, No. Supp. 1, Nov. 6, 2019, p. 757,
Retrieved from the Internet: URL:https://jitc.bmj.com/content/7/
Suppl_1/283, 1 page.

* cited by examiner

Binding to SIRPα v1

248G3F6 $EC_{50}$ = 18.2 ng/ml
300A6A6 $EC_{50}$ = 12.1 ng/ml

Binding to SIRPα v2

248G3F6 $EC_{50}$ = 13.6 ng/ml
300A6A6 $EC_{50}$ = 10.5 ng/ml

248G3F6 $IC_{50}$ = 355.8 ng/ml
300A6A6 $IC_{50}$ = 383.1 ng/ml

SEQUENCE LISTING

```
<160> NUMBER OF SEQ ID NOS: 118

<210> SEQ ID NO 1
<211> LENGTH: 114
<212> TYPE: PRT
<213> ORGANISM: Artificial Sequence
<220> FEATURE:
<223> OTHER INFORMATION: Synthetic

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Phe Glu Asp Thr
            20                  25                  30

Tyr Met His Trp Val Lys Gln Arg Pro Asp Gln Gly Leu Glu Trp Ile
        35                  40                  45

Gly Arg Ile Asp Pro Ala Asp Gly Asp Thr Lys Tyr Asn Pro Lys Phe
    50                  55                  60

Gln Asp Lys Ala Thr Ile Thr Val Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Gly Asn Tyr Val Asn Trp Gly Gln Gly Thr Thr Leu Thr Val
                100                 105                 110

Ser Ser

<210> SEQ ID NO 2
<211> LENGTH: 108
<212> TYPE: PRT
<213> ORGANISM: Artificial Sequence
<220> FEATURE:
<223> OTHER INFORMATION: Synthetic

<400> SEQUENCE: 2

Gln Ile Val Leu Ile Gln Ser Pro Ala Ile Met Ser Ala Ser Pro Gly
1               5                   10                  15

Glu Arg Val Thr Leu Thr Cys Arg Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Tyr Ser Tyr Pro
                85                  90                  95

Arg Thr Phe Gly Gly Gly Thr Lys Leu Glu Ile Lys
                100                 105
```

-continued

```
<210> SEQ ID NO 3
<211> LENGTH: 118
<212> TYPE: PRT
<213> ORGANISM: Artificial Sequence
<220> FEATURE:
<223> OTHER INFORMATION: Synthetic

<400> SEQUENCE: 3

Gln Val Gln Leu Gln Gln Ser Gly Thr Glu Leu Val Lys Pro Gly Ser
1               5                   10                  15

Ser Val Lys Ile Ser Cys Lys Ala Ser Gly Tyr Thr Phe Thr Ser Asn
            20                  25                  30

Tyr Ile His Trp Ile Arg Gln Gln Pro Gly Asn Gly Leu Glu Trp Ile
        35                  40                  45

Gly Trp Ile Tyr Pro Gly Asp Gly Asp Thr Asn Tyr Asn Gln Lys Phe
    50                  55                  60

Asn Gly Lys Ala Thr Leu Thr Ala Asp Lys Ser Ser Ser Thr Ala Tyr
65                  70                  75                  80

Met Gln Leu Ser Ser Leu Thr Ser Glu Asp Tyr Ala Val Tyr Phe Cys
                85                  90                  95

Ala Ile Asn Tyr Gly Gly Ile Trp Phe Ala Tyr Trp Gly Gln Gly Thr
            100                 105                 110

Leu Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Synthetic

<400> SEQUENCE: 4

Asp Ile Gln Met Thr Gln Ser Pro Ser Ser Met Ser Ala Ser Leu Gly
1               5                   10                  15

Asp Arg Val Thr Ile Thr Cys Gln Ala Ser Gln Asp Ile Gly Asn Lys
            20                  25                  30

Leu Ile Trp Phe Gln Gln Lys Pro Gly Lys Ser Pro Arg Leu Met Ile
        35                  40                  45

His Tyr Val Thr Asn Leu Pro Gly Gly Val Pro Leu Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Met Ala Asp Tyr Tyr Cys Leu Gln Tyr Lys Gln Asn Pro Leu
                85                  90                  95

Thr Phe Gly Ser Gly Thr Lys Leu Glu Ile Lys
            100                 105

<210> SEQ ID NO 5
<211> LENGTH: 123
<212> TYPE: PRT
<213> ORGANISM: Artificial Sequence
<220> FEATURE:
<223> OTHER INFORMATION: Synthetic

<400> SEQUENCE: 5

Gln Val Thr Leu Lys Glu Ser Gly Pro Gly Ile Leu Gln Pro Ser Gln
1               5                   10                  15
```

```
Thr Leu Ser Leu Thr Cys Ser Phe Ser Gly Phe Ser Leu Asn Thr Tyr
            20                  25                  30

Asp Ile Gly Met Gly Trp Ile Arg Gln Pro Ser Gly Lys Gly Leu Glu
        35                  40                  45

Trp Leu Ala His Ile Trp Trp Asn Asp Arg Glu Tyr Tyr Asn Ser Ala
    50                  55                  60

Leu Gln Ser Arg Val Thr Ile Ser Lys Asp Thr Ser Asn Thr Gln Val
65                  70                  75                  80

Phe Leu Lys Ile Ala Ser Val Asp Thr Ala Asp Thr Ala Thr Tyr Tyr
                85                  90                  95

Cys Val Arg Ile Asp Tyr Phe Gly Ser Gly Gln Ala Trp Phe Thr Tyr
            100                 105                 110

Trp Gly Gln Gly Thr Leu Val Thr Val Ser Ala
        115                 120
```

```
<210> SEQ ID NO 6
<211> LENGTH: 108
<212> TYPE: PRT
<213> ORGANISM: Artificial Sequence
<220> FEATURE:
<223> OTHER INFORMATION: Synthetic

<400> SEQUENCE: 6
```

```
Glu Ile Val Leu Thr Gln Ser Pro Pro Thr Met Ala Ala Ser Pro Gly
1               5                   10                  15

Glu Lys Ile Thr Ile Thr Cys Ser Ser Ser Ser Thr Ile Ser Ser Thr
            20                  25                  30

Tyr Leu His Trp Tyr Gln Gln Lys Pro Gly Phe Ser Pro Lys Leu Leu
        35                  40                  45

Ile Ser Gly Thr Ser Asn Leu Ala Ser Gly Val Pro Pro Arg Phe Ser
    50                  55                  60

Gly Ser Gly Ser Gly Thr Ser Tyr Ser Leu Thr Ile Gly Thr Leu Glu
65                  70                  75                  80

Ala Glu Asp Val Ala Thr Tyr Tyr Cys Gln Gln Gly Ser Arg Ile Pro
                85                  90                  95

Phe Thr Phe Gly Ser Gly Thr Lys Leu Glu Ile Lys
            100                 105
```

```
<210> SEQ ID NO 7
<211> LENGTH: 113
<212> TYPE: PRT
<213> ORGANISM: Artificial Sequence
<220> FEATURE:
<223> OTHER INFORMATION: Synthetic

<400> SEQUENCE: 7
```

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95
```

```
Ser Arg Ser Trp Ala Tyr Trp Gly Gln Gly Thr Thr Leu Thr Val Ser
            100                 105                 110

Ser

<210> SEQ ID NO 8
<211> LENGTH: 108
<212> TYPE: PRT
<213> ORGANISM: Artificial Sequence
<220> FEATURE:
<223> OTHER INFORMATION: Synthetic

<400> SEQUENCE: 8

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Ser
            20                  25                  30

Tyr Leu Tyr Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
            85                  90                  95

Arg Thr Phe Gly Gly Gly Thr Lys Leu Glu Ile Lys
            100                 105

<210> SEQ ID NO 9
<211> LENGTH: 120
<212> TYPE: PRT
<213> ORGANISM: Artificial Sequence
<220> FEATURE:
<223> OTHER INFORMATION: Synthetic

<400> SEQUENCE: 9

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Val
        35                  40                  45

Gly Arg Ile Asp Pro Ala Asn Val Asn Thr Ile Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
            85                  90                  95

Ala Arg Val Gly Ala Tyr Asp Gly Tyr Asp Phe Asp Tyr Trp Gly Gln
            100                 105                 110

Gly Thr Thr Leu Thr Val Ser Ser
        115                 120

<210> SEQ ID NO 10
<211> LENGTH: 111
<212> TYPE: PRT
<213> ORGANISM: Artificial Sequence
<220> FEATURE:
<223> OTHER INFORMATION: Synthetic
```

-continued

<400> SEQUENCE: 10

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Asn Asn
            85                  90                  95

Glu Asp Pro Leu Thr Phe Gly Ala Gly Thr Lys Leu Glu Leu Lys
            100                 105                 110
```

<210> SEQ ID NO 11
<211> LENGTH: 120
<212> TYPE: PRT
<213> ORGANISM: Artificial Sequence
<220> FEATURE:
<223> OTHER INFORMATION: Synthetic

<400> SEQUENCE: 11

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
            85                  90                  95

Ala Arg Ser Tyr Tyr Asp Tyr Asp Gly Ser Phe Asp Tyr Trp Gly Gln
            100                 105                 110

Gly Thr Thr Leu Thr Val Ser Ser
        115                 120
```

<210> SEQ ID NO 12
<211> LENGTH: 107
<212> TYPE: PRT
<213> ORGANISM: Artificial Sequence
<220> FEATURE:
<223> OTHER INFORMATION: Synthetic

<400> SEQUENCE: 12

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Thr Ala
            20                  25                  30

Val Ala Trp Tyr Gln Gln Lys Ser Gly Gln Ser Pro Lys Leu Leu Ile
        35                  40                  45

Tyr Ser Ala Ser Tyr Arg Tyr Thr Gly Asp Pro Asp Arg Phe Thr Gly
    50                  55                  60
```

-continued

```
Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 13
<211> LENGTH: 114
<212> TYPE: PRT
<213> ORGANISM: Artificial Sequence
<220> FEATURE:
<223> OTHER INFORMATION: Synthetic

<400> SEQUENCE: 13

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Phe Glu Asp Thr
                20                  25                  30

Tyr Ile His Trp Val Lys Gln Arg Pro Asp Gln Gly Leu Glu Trp Ile
            35                  40                  45

Gly Arg Ile Asp Pro Ala Asp Gly Asp Thr Lys His Asn Pro Lys Phe
            50                  55                  60

His Asp Lys Ala Thr Val Thr Val Asp Thr Ser Ser Asn Thr Ala Tyr
65                  70                  75                  80

Leu Glu Leu Ser Ser Leu Thr Ser Glu Asp Thr Ala Val Tyr Tyr Cys
                85                  90                  95

Val Arg Gly Asn Tyr Val Asn Trp Gly Gln Gly Thr Thr Leu Thr Val
            100                 105                 110

Ser Ser

<210> SEQ ID NO 14
<211> LENGTH: 108
<212> TYPE: PRT
<213> ORGANISM: Artificial Sequence
<220> FEATURE:
<223> OTHER INFORMATION: Synthetic

<400> SEQUENCE: 14

Gln Ile Val Leu Ile Gln Ser Pro Ala Ile Met Ser Ala Ser Pro Gly
1               5                   10                  15

Glu Arg Val Thr Leu Thr Cys Arg Ala Ser Ser Ser Val Thr Ser Ser
                20                  25                  30

Tyr Leu Tyr Trp Tyr Gln Gln Lys Pro Gly Ser Ser Pro Lys Leu Trp
            35                  40                  45

Ile Tyr Ser Ala Ser Asn Leu Ala Ser Gly Val Pro Ala Arg Phe Ser
            50                  55                  60

Gly Ser Gly Ser Gly Thr Ser Tyr Ser Leu Thr Ile Ser Ser Val Glu
65                  70                  75                  80

Ala Glu Asp Ala Ala Ser Tyr Phe Cys His Gln Trp Tyr Ser Tyr Pro
                85                  90                  95

Arg Thr Phe Gly Gly Gly Thr Lys Leu Glu Ile Lys
            100                 105

<210> SEQ ID NO 15
<211> LENGTH: 5
<212> TYPE: PRT
<213> ORGANISM: Artificial Sequence
<220> FEATURE:
```

<223> OTHER INFORMATION: Synthetic

<400> SEQUENCE: 15

Asp Thr Tyr Met His
1               5

<210> SEQ ID NO 16
<211> LENGTH: 17
<212> TYPE: PRT
<213> ORGANISM: Artificial Sequence
<220> FEATURE:
<223> OTHER INFORMATION: Synthetic

<400> SEQUENCE: 16

Arg Ile Asp Pro Ala Asp Gly Asp Thr Lys Tyr Asn Pro Lys Phe Gln
1               5                   10                  15

Asp

<210> SEQ ID NO 17
<211> LENGTH: 5
<212> TYPE: PRT
<213> ORGANISM: Artificial Sequence
<220> FEATURE:
<223> OTHER INFORMATION: Synthetic

<400> SEQUENCE: 17

Gly Asn Tyr Val Asn
1               5

<210> SEQ ID NO 18
<211> LENGTH: 12
<212> TYPE: PRT
<213> ORGANISM: Artificial Sequence
<220> FEATURE:
<223> OTHER INFORMATION: Synthetic

<400> SEQUENCE: 18

Arg Ala Ser Ser Ser Val Ser Ser Ser Tyr Leu Tyr
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic

<400> SEQUENCE: 19

Ser Thr Ser Asn Leu Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

His Gln Trp Tyr Ser Tyr Pro Arg Thr
1               5

<210> SEQ ID NO 21
<211> LENGTH: 17
<212> TYPE: PRT
<213> ORGANISM: Artificial Sequence
<220> FEATURE:
<223> OTHER INFORMATION: Synthetic

<400> SEQUENCE: 21

Arg Ile Asp Pro Ala Glu Gly Asp Thr Lys Tyr Asn Pro Lys Phe Gln
1               5                   10                  15

Asp

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Arg Ile Asp Pro Ala Asp Ala Asp Thr Lys Tyr Asn Pro Lys Phe Gln
1               5                   10                  15

Asp

<210> SEQ ID NO 23
<211> LENGTH: 114
<212> TYPE: PRT
<213> ORGANISM: Artificial Sequence
<220> FEATURE:
<223> OTHER INFORMATION: Synthetic

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Glu Asp Thr
                20                  25                  30

Tyr Met His Trp Val Arg Gln Ala Pro Gly Gln Gly Leu Glu Trp Met
            35                  40                  45

Gly Arg Ile Asp Pro Ala Asp Gly Asp Thr Lys Tyr Asn Pro Lys Phe
        50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Val Asn Trp Gly Gln Gly Thr Thr Val Thr Val
            100                 105                 110

Ser Ser

<210> SEQ ID NO 24
<211> LENGTH: 114
<212> TYPE: PRT
<213> ORGANISM: Artificial Sequence
<220> FEATURE:
<223> OTHER INFORMATION: Synthetic

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Glu Asp Thr
                20                  25                  30

Tyr Met His Trp Val Arg Gln Ala Pro Gly Gln Gly Leu Glu Trp Met
            35                  40                  45

Gly Arg Ile Asp Pro Ala Asp Gly Asp Thr Lys Tyr Asn Pro Lys Phe
        50                  55                  60

```
Gln Asp Arg Val Thr Met Thr Val Asp Thr Ser Thr Asn Thr Ala Tyr
65              70              75              80

Met Glu Leu Ser Ser Leu Arg Ser Glu Asp Thr Ala Val Tyr Tyr Cys
                85              90              95

Val Arg Gly Asn Tyr Val Asn Trp Gly Gln Gly Thr Thr Val Thr Val
            100             105             110

Ser Ser

<210> SEQ ID NO 25
<211> LENGTH: 114
<212> TYPE: PRT
<213> ORGANISM: Artificial Sequence
<220> FEATURE:
<223> OTHER INFORMATION: Synthetic

<400> SEQUENCE: 25

Gln Val Gln Leu Val Gln Ser Gly Ala Glu Val Lys Lys Pro Gly Ala
1               5               10              15

Ser Val Lys Val Ser Cys Lys Ala Ser Gly Phe Asn Phe Glu Asp Thr
            20              25              30

Tyr Met His Trp Val Arg Gln Ala Pro Gly Gln Gly Leu Glu Trp Met
        35              40              45

Gly Arg Ile Asp Pro Ala Asp Gly Asp Thr Lys Tyr Asn Pro Lys Phe
    50              55              60

Gln Asp Arg Val Thr Ile Thr Val Asp Thr Ser Thr Asn Thr Ala Tyr
65              70              75              80

Met Glu Leu Ser Ser Leu Arg Ser Glu Asp Thr Ala Val Tyr Tyr Cys
                85              90              95

Val Arg Gly Asn Tyr Val Asn Trp Gly Gln Gly Thr Thr Val Thr Val
            100             105             110

Ser Ser

<210> SEQ ID NO 26
<211> LENGTH: 114
<212> TYPE: PRT
<213> ORGANISM: Artificial Sequence
<220> FEATURE:
<223> OTHER INFORMATION: Synthetic

<400> SEQUENCE: 26

Gln Val Gln Leu Val Gln Ser Gly Ala Glu Val Lys Lys Pro Gly Ala
1               5               10              15

Ser Val Lys Val Ser Cys Lys Ala Ser Gly Phe Asn Phe Glu Asp Thr
            20              25              30

Tyr Met His Trp Val Arg Gln Ala Pro Gly Gln Gly Leu Glu Trp Met
        35              40              45

Gly Arg Ile Asp Pro Ala Glu Gly Asp Thr Lys Tyr Asn Pro Lys Phe
    50              55              60

Gln Asp Arg Val Thr Ile Thr Val Asp Thr Ser Thr Asn Thr Ala Tyr
65              70              75              80

Met Glu Leu Ser Ser Leu Arg Ser Glu Asp Thr Ala Val Tyr Tyr Cys
                85              90              95

Val Arg Gly Asn Tyr Val Asn Trp Gly Gln Gly Thr Thr Val Thr Val
            100             105             110

Ser Ser
```

```
<210> SEQ ID NO 27
<211> LENGTH: 114
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Glu Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asp Ala Asp Thr Lys Tyr Asn Pro Lys Phe
    50                  55                  60

Gln Asp Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Asn Tyr Val Asn Trp Gly Gln Gly Thr Thr Val Thr Val
                100                 105                 110

Ser Ser

<210> SEQ ID NO 28
<211> LENGTH: 108
<212> TYPE: PRT
<213> ORGANISM: Artificial Sequence
<220> FEATURE:
<223> OTHER INFORMATION: Synthetic

<400> SEQUENCE: 28

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30

Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Trp Tyr Ser Tyr Pro
                85                  90                  95

Arg Thr Phe Gly Gly Gly Thr Lys Val Glu Ile Lys
                100                 105

<210> SEQ ID NO 29
<211> LENGTH: 108
<212> TYPE: PRT
<213> ORGANISM: Artificial Sequence
<220> FEATURE:
<223> OTHER INFORMATION: Synthetic

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Ser Ser
            20                  25                  30
```

```
Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Ala Ala Val Tyr Phe Cys His Gln Trp Tyr Ser Tyr Pro
                85                  90                  95

Arg Thr Phe Gly Gly Gly Thr Lys Val Glu Ile Lys
            100                 105
```

<210> SEQ ID NO 30
<211> LENGTH: 5
<212> TYPE: PRT
<213> ORGANISM: Artificial Sequence
<220> FEATURE:
<223> OTHER INFORMATION: Synthetic

<400> SEQUENCE: 30

```
Ser Asn Tyr Ile His
1               5
```

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

```
Trp Ile Tyr Pro Gly Asp Gly Asp Thr Asn Tyr Asn Gln Lys Phe Asn
1               5                   10                  15

Gly
```

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

```
Asn Tyr Gly Gly Ile Trp Phe Ala Tyr
1               5
```

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

```
Gln Ala Ser Gln Asp Ile Gly Asn Lys Leu Ile
1               5                   10
```

<210> SEQ ID NO 34
<211> LENGTH: 7
<212> TYPE: PRT
<213> ORGANISM: Artificial Sequence
<220> FEATURE:
<223> OTHER INFORMATION: Synthetic

<400> SEQUENCE: 34

Tyr Val Thr Asn Leu Pro Gly
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic

<400> SEQUENCE: 35

Leu Gln Tyr Lys Gln Asn Pro Leu Thr
1               5

<210> SEQ ID NO 36
<211> LENGTH: 17
<212> TYPE: PRT
<213> ORGANISM: Artificial Sequence
<220> FEATURE:
<223> OTHER INFORMATION: Synthetic

<400> SEQUENCE: 36

Trp Ile Tyr Pro Gly Glu Gly Asp Thr Asn Tyr Asn Gln Lys Phe Asn
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Trp Ile Tyr Pro Gly Asp Ala Asp Thr Asn Tyr Asn Gln Lys Phe Asn
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: Synthetic

<400> SEQUENCE: 38

Trp Ile Tyr Pro Gly Asp Gly Asp Thr Asn Tyr Asn Gln Lys Phe Gln
1               5                   10                  15

Gly

<210> SEQ ID NO 39
<211> LENGTH: 118
<212> TYPE: PRT
<213> ORGANISM: Artificial Sequence
<220> FEATURE:
<223> OTHER INFORMATION: Synthetic

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Asn
                20                  25                  30

```
Tyr Ile His Trp Val Arg Gln Ala Pro Gly Gln Gly Leu Glu Trp Met
        35                  40                  45

Gly Trp Ile Tyr Pro Gly Asp Gly Asp Thr Asn Tyr Asn Gln Lys Phe
    50                  55                  60

Asn Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Gly Gly Ile Trp Phe Ala Tyr Trp Gly Gln Gly Thr
                100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetic

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Asn
                20                  25                  30

Tyr Ile His Trp Val Arg Gln Ala Pro Gly Gln Gly Leu Glu Trp Met
        35                  40                  45

Gly Trp Ile Tyr Pro Gly Asp Gly Asp Thr Asn Tyr Asn Gln Lys Phe
    50                  55                  60

Asn Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Tyr Gly Gly Ile Trp Phe Ala Tyr Trp Gly Gln Gly Thr
                100                 105                 110

Leu Val Thr Val Ser Ser
        115

<210> SEQ ID NO 41
<211> LENGTH: 118
<212> TYPE: PRT
<213> ORGANISM: Artificial Sequence
<220> FEATURE:
<223> OTHER INFORMATION: Synthetic

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Asn
                20                  25                  30

Tyr Ile His Trp Val Arg Gln Ala Pro Gly Gln Gly Leu Glu Trp Met
        35                  40                  45

Gly Trp Ile Tyr Pro Gly Asp Gly Asp Thr Asn Tyr Asn Gln Lys Phe
    50                  55                  60

Asn Gly Arg Val Thr Leu Thr Ala Asp Lys Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Ile Asn Tyr Gly Gly Ile Trp Phe Ala Tyr Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Synthetic

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Asn
            20                  25                  30

Tyr Ile His Trp Val Arg Gln Ala Pro Gly Gln Gly Leu Glu Trp Met
        35                  40                  45

Gly Trp Ile Tyr Pro Gly Glu Gly Asp Thr Asn Tyr Asn Gln Lys Phe
    50                  55                  60

Asn Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Tyr Gly Gly Ile Trp Phe Ala Tyr Trp Gly Gln Gly Thr
            100                 105                 110

Leu Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Synthetic

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Asn
            20                  25                  30

Tyr Ile His Trp Val Arg Gln Ala Pro Gly Gln Gly Leu Glu Trp Met
        35                  40                  45

Gly Trp Ile Tyr Pro Gly Asp Ala Asp Thr Asn Tyr Asn Gln Lys Phe
    50                  55                  60

Asn Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Tyr Gly Gly Ile Trp Phe Ala Tyr Trp Gly Gln Gly Thr
            100                 105                 110

Leu Val Thr Val Ser Ser
        115
```

-continued

```
<210> SEQ ID NO 44
<211> LENGTH: 118
<212> TYPE: PRT
<213> ORGANISM: Artificial Sequence
<220> FEATURE:
<223> OTHER INFORMATION: Synthetic

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Asn
            20                  25                  30

Tyr Ile His Trp Val Arg Gln Ala Pro Gly Gln Gly Leu Glu Trp Met
        35                  40                  45

Gly Trp Ile Tyr Pro Gly Asp Gly Asp Thr Asn Tyr Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Tyr Gly Gly Ile Trp Phe Ala Tyr Trp Gly Gln Gly Thr
            100                 105                 110

Leu Val Thr Val Ser Ser
        115

<210> SEQ ID NO 45
<211> LENGTH: 107
<212> TYPE: PRT
<213> ORGANISM: Artificial Sequence
<220> FEATURE:
<223> OTHER INFORMATION: Synthetic

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Lys
            20                  25                  30

Leu Ile Trp Tyr Gln Gln Lys Pro Gly Lys Ala Pro Lys Leu Leu Ile
        35                  40                  45

Tyr Tyr Val Thr Asn Leu Pro Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Lys Gln Asn Pro Leu
                85                  90                  95

Thr Phe Gly Gln Gly Thr Lys Leu Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: Synthetic

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Lys
            20                  25                  30
```

-continued

```
Leu Ile Trp Phe Gln Gln Lys Pro Gly Lys Ala Pro Lys Leu Leu Ile
        35                  40                  45

His Tyr Val Thr Asn Leu Pro Gly Gly Val Pro Ser Arg Phe Ser Gly
        50                  55                  60

Ser Arg Ser Gly Ser Asp Tyr Thr Leu Thr Ile Ser Ser Leu Gln Pro
65                  70                  75                  80

Glu Asp Phe Ala Thr Tyr Tyr Cys Leu Gln Tyr Lys Gln Asn Pro Leu
                85                  90                  95

Thr Phe Gly Gln Gly Thr Lys Leu Glu Ile Lys
            100                 105

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Thr Tyr Asp Ile Gly Met Gly
1               5

<210> SEQ ID NO 48
<211> LENGTH: 16
<212> TYPE: PRT
<213> ORGANISM: Artificial Sequence
<220> FEATURE:
<223> OTHER INFORMATION: Synthetic

<400> SEQUENCE: 48

His Ile Trp Trp Asn Asp Arg Glu Tyr Tyr Asn Ser Ala Leu Gln Ser
1               5                   10                  15

<210> SEQ ID NO 49
<211> LENGTH: 13
<212> TYPE: PRT
<213> ORGANISM: Artificial Sequence
<220> FEATURE:
<223> OTHER INFORMATION: Synthetic

<400> SEQUENCE: 49

Ile Asp Tyr Phe Gly Ser Gly Gln Ala Trp Phe Thr Tyr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic

<400> SEQUENCE: 50

Ser Ser Ser Ser Thr Ile Ser Ser Thr Tyr Leu His
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic
```

-continued

<400> SEQUENCE: 51

Gly Thr Ser Asn Leu Ala Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Gln Gln Gly Ser Arg Ile Pro Phe Thr
1               5

<210> SEQ ID NO 53
<211> LENGTH: 16
<212> TYPE: PRT
<213> ORGANISM: Artificial Sequence
<220> FEATURE:
<223> OTHER INFORMATION: Synthetic

<400> SEQUENCE: 53

His Ile Trp Trp Asn Asp Arg Glu Tyr Tyr Ser Ser Ala Leu Gln Ser
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Synthetic

<400> SEQUENCE: 54

His Ile Trp Trp Asn Asp Arg Glu Tyr Tyr Asn Pro Ala Leu Gln Ser
1               5                   10                  15

<210> SEQ ID NO 55
<211> LENGTH: 123
<212> TYPE: PRT
<213> ORGANISM: Artificial Sequence
<220> FEATURE:
<223> OTHER INFORMATION: Synthetic

<400> SEQUENCE: 55

Gln Leu Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Asn Thr Tyr
                20                  25                  30

Asp Ile Gly Met Gly Trp Ile Arg Gln Pro Pro Gly Lys Gly Leu Glu
            35                  40                  45

Trp Ile Gly His Ile Trp Trp Asn Asp Arg Glu Tyr Tyr Asn Ser Ala
        50                  55                  60

Leu Gln Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ile Asp Tyr Phe Gly Ser Gly Gln Ala Trp Phe Thr Tyr
            100                 105                 110

Trp Gly Gln Gly Thr Leu Val Thr Val Ser Ser
        115                 120

-continued

```
<210> SEQ ID NO 56
<211> LENGTH: 123
<212> TYPE: PRT
<213> ORGANISM: Artificial Sequence
<220> FEATURE:
<223> OTHER INFORMATION: Synthetic

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Phe Ser Gly Phe Ser Leu Asn Thr Tyr
            20                  25                  30

Asp Ile Gly Met Gly Trp Ile Arg Gln Pro Pro Gly Lys Gly Leu Glu
        35                  40                  45

Trp Ile Gly His Ile Trp Trp Asn Asp Arg Glu Tyr Tyr Asn Ser Ala
    50                  55                  60

Leu Gln Ser Arg Val Thr Ile Ser Lys Asp Thr Ser Lys Thr Gln Val
65                  70                  75                  80

Ser Leu Lys Leu Ser Ser Val Thr Ala Ala Asp Thr Ala Val Tyr Tyr
                85                  90                  95

Cys Val Arg Ile Asp Tyr Phe Gly Ser Gly Gln Ala Trp Phe Thr Tyr
            100                 105                 110

Trp Gly Gln Gly Thr Leu Val Thr Val Ser Ser
        115                 120

<210> SEQ ID NO 57
<211> LENGTH: 123
<212> TYPE: PRT
<213> ORGANISM: Artificial Sequence
<220> FEATURE:
<223> OTHER INFORMATION: Synthetic

<400> SEQUENCE: 57

Gln Val Gln Leu Gln Glu Ser Gly Pro Gly Leu Val Lys Pro Ser Glu
1               5                   10                  15

Thr Leu Ser Leu Thr Cys Thr Phe Ser Gly Phe Ser Leu Asn Thr Tyr
            20                  25                  30

Asp Ile Gly Met Gly Trp Ile Arg Gln Pro Pro Gly Lys Gly Leu Glu
        35                  40                  45

Trp Ile Ala His Ile Trp Trp Asn Asp Arg Glu Tyr Tyr Asn Ser Ala
    50                  55                  60

Leu Gln Ser Arg Val Thr Ile Ser Lys Asp Thr Ser Lys Thr Gln Val
65                  70                  75                  80

Ser Leu Lys Leu Ser Ser Val Thr Ala Ala Asp Thr Ala Val Tyr Tyr
                85                  90                  95

Cys Val Arg Ile Asp Tyr Phe Gly Ser Gly Gln Ala Trp Phe Thr Tyr
            100                 105                 110

Trp Gly Gln Gly Thr Leu Val Thr Val Ser Ser
        115                 120

<210> SEQ ID NO 58
<211> LENGTH: 123
<212> TYPE: PRT
<213> ORGANISM: Artificial Sequence
<220> FEATURE:
<223> OTHER INFORMATION: Synthetic
```

-continued

```
<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Thr Phe Ser Gly Phe Ser Leu Ser Thr Tyr
            20                  25                  30

Asp Ile Gly Met Gly Trp Ile Arg Gln Pro Pro Gly Lys Gly Leu Glu
        35                  40                  45

Trp Ile Ala His Ile Trp Trp Asn Asp Arg Glu Tyr Tyr Asn Ser Ala
    50                  55                  60

Leu Gln Ser Arg Val Thr Ile Ser Lys Asp Thr Ser Lys Thr Gln Val
65                  70                  75                  80

Ser Leu Lys Leu Ser Ser Val Thr Ala Ala Asp Thr Ala Val Tyr Tyr
            85                  90                  95

Cys Val Arg Ile Asp Tyr Phe Gly Ser Gly Gln Ala Trp Phe Thr Tyr
            100                 105                 110

Trp Gly Gln Gly Thr Leu Val Thr Val Ser Ser
        115                 120

<210> SEQ ID NO 59
<211> LENGTH: 123
<212> TYPE: PRT
<213> ORGANISM: Artificial Sequence
<220> FEATURE:
<223> OTHER INFORMATION: Synthetic

<400> SEQUENCE: 59

Gln Val Gln Leu Gln Glu Ser Gly Pro Gly Leu Val Lys Pro Ser Glu
1               5                   10                  15

Thr Leu Ser Leu Thr Cys Thr Phe Ser Gly Phe Ser Leu Asn Thr Tyr
            20                  25                  30

Asp Ile Gly Met Gly Trp Ile Arg Gln Pro Pro Gly Lys Gly Leu Glu
        35                  40                  45

Trp Ile Ala His Ile Trp Trp Asn Asp Arg Glu Tyr Tyr Ser Ser Ala
    50                  55                  60

Leu Gln Ser Arg Val Thr Ile Ser Lys Asp Thr Ser Lys Thr Gln Val
65                  70                  75                  80

Ser Leu Lys Leu Ser Ser Val Thr Ala Ala Asp Thr Ala Val Tyr Tyr
            85                  90                  95

Cys Val Arg Ile Asp Tyr Phe Gly Ser Gly Gln Ala Trp Phe Thr Tyr
            100                 105                 110

Trp Gly Gln Gly Thr Leu Val Thr Val Ser Ser
        115                 120

<210> SEQ ID NO 60
<211> LENGTH: 123
<212> TYPE: PRT
<213> ORGANISM: Artificial Sequence
<220> FEATURE:
<223> OTHER INFORMATION: Synthetic

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Thr Phe Ser Gly Phe Ser Leu Asn Thr Tyr
            20                  25                  30

Asp Ile Gly Met Gly Trp Ile Arg Gln Pro Pro Gly Lys Gly Leu Glu
        35                  40                  45
```

```
Trp Ile Ala His Ile Trp Trp Asn Asp Arg Glu Tyr Tyr Asn Pro Ala
    50                  55                  60

Leu Gln Ser Arg Val Thr Ile Ser Lys Asp Thr Ser Lys Thr Gln Val
65                  70                  75                  80

Ser Leu Lys Leu Ser Ser Val Thr Ala Ala Asp Thr Ala Val Tyr Tyr
                85                  90                  95

Cys Val Arg Ile Asp Tyr Phe Gly Ser Gly Gln Ala Trp Phe Thr Tyr
                100                 105                 110

Trp Gly Gln Gly Thr Leu Val Thr Val Ser Ser
        115                 120
```

```
<210> SEQ ID NO 61
<211> LENGTH: 108
<212> TYPE: PRT
<213> ORGANISM: Artificial Sequence
<220> FEATURE:
<223> OTHER INFORMATION: Synthetic

<400> SEQUENCE: 61

Glu Ile Val Leu Thr Gln Ser Pro Gly Thr Leu Ser Leu Ser Pro Gly
1                   5                   10                  15

Glu Arg Ala Thr Leu Ser Cys Ser Ser Ser Ser Thr Ile Ser Ser Thr
                20                  25                  30

Tyr Leu His Trp Tyr Gln Gln Lys Pro Gly Gln Ala Pro Arg Leu Leu
            35                  40                  45

Ile Tyr Gly Thr Ser Asn Leu Ala Ser Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ser Arg Ile Pro
                85                  90                  95

Phe Thr Phe Gly Gln Gly Thr Lys Leu Glu Ile Lys
                100                 105
```

```
<210> SEQ ID NO 62
<211> LENGTH: 108
<212> TYPE: PRT
<213> ORGANISM: Artificial Sequence
<220> FEATURE:
<223> OTHER INFORMATION: Synthetic

<400> SEQUENCE: 62

Glu Ile Val Leu Thr Gln Ser Pro Gly Thr Leu Ser Leu Ser Pro Gly
1                   5                   10                  15

Glu Arg Ala Thr Leu Ser Cys Ser Ser Ser Ser Thr Ile Ser Ser Thr
                20                  25                  30

Tyr Leu His Trp Tyr Gln Gln Lys Pro Gly Gln Ala Pro Arg Leu Leu
            35                  40                  45

Ile Ser Gly Thr Ser Asn Leu Ala Ser Gly Ile Pro Asp Arg Phe Ser
        50                  55                  60

Gly Ser Gly Ser Gly Thr Asp Tyr Thr Leu Thr Ile Ser Arg Leu Glu
65                  70                  75                  80

Pro Glu Asp Val Ala Val Tyr Tyr Cys Gln Gln Gly Ser Arg Ile Pro
                85                  90                  95

Phe Thr Phe Gly Gln Gly Thr Lys Leu Glu Ile Lys
                100                 105
```

-continued

```
<210> SEQ ID NO 63
<211> LENGTH: 5
<212> TYPE: PRT
<213> ORGANISM: Artificial Sequence
<220> FEATURE:
<223> OTHER INFORMATION: Synthetic

<400> SEQUENCE: 63

Asp Tyr Tyr Met His
1               5

<210> SEQ ID NO 64
<211> LENGTH: 17
<212> TYPE: PRT
<213> ORGANISM: Artificial Sequence
<220> FEATURE:
<223> OTHER INFORMATION: Synthetic

<400> SEQUENCE: 64

Arg Ile Asp Pro Glu Asp Gly Glu Thr Lys Tyr Ala Pro Lys Phe Gln
1               5                   10                  15

Gly

<210> SEQ ID NO 65
<211> LENGTH: 4
<212> TYPE: PRT
<213> ORGANISM: Artificial Sequence
<220> FEATURE:
<223> OTHER INFORMATION: Synthetic

<400> SEQUENCE: 65

Ser Trp Ala Tyr
1

<210> SEQ ID NO 66
<211> LENGTH: 12
<212> TYPE: PRT
<213> ORGANISM: Artificial Sequence
<220> FEATURE:
<223> OTHER INFORMATION: Synthetic

<400> SEQUENCE: 66

Ser Ala Ser Ser Ser Val Ser Ser Ser Tyr Leu Tyr
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic

<400> SEQUENCE: 67

Ser Thr Ser Asn Leu Ala Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

His Gln Trp Ser Ser Tyr Pro Arg Thr
1               5
```

<210> SEQ ID NO 69
<211> LENGTH: 113
<212> TYPE: PRT
<213> ORGANISM: Artificial Sequence
<220> FEATURE:
<223> OTHER INFORMATION: Synthetic

<400> SEQUENCE: 69

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Tyr
                20                  25                  30

Tyr Met His Trp Val Gln Gln Ala Pro Gly Lys Gly Leu Glu Trp Met
            35                  40                  45

Gly Arg Ile Asp Pro Glu Asp Gly Glu Thr Lys Tyr Ala Pro Lys Phe
        50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Trp Ala Tyr Trp Gly Gln Gly Thr Thr Val Thr Val Ser
            100                 105                 110

Ser

<210> SEQ ID NO 70
<211> LENGTH: 113
<212> TYPE: PRT
<213> ORGANISM: Artificial Sequence
<220> FEATURE:
<223> OTHER INFORMATION: Synthetic

<400> SEQUENCE: 70

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Tyr
                20                  25                  30

Tyr Met His Trp Val Gln Gln Ala Pro Gly Lys Gly Leu Glu Trp Met
            35                  40                  45

Gly Arg Ile Asp Pro Glu Asp Gly Glu Thr Lys Tyr Ala Pro Lys Phe
        50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Trp Ala Tyr Trp Gly Gln Gly Thr Thr Val Thr Val Ser
            100                 105                 110

Ser

<210> SEQ ID NO 71
<211> LENGTH: 113
<212> TYPE: PRT
<213> ORGANISM: Artificial Sequence
<220> FEATURE:
<223> OTHER INFORMATION: Synthetic

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Met
        35                  40                  45

Gly Arg Ile Asp Pro Glu Asp Gly Glu Thr Lys Tyr Ala Pro Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Trp Ala Tyr Trp Gly Gln Gly Thr Thr Val Thr Val Ser
            100                 105                 110

Ser

<210> SEQ ID NO 72
<211> LENGTH: 113
<212> TYPE: PRT
<213> ORGANISM: Artificial Sequence
<220> FEATURE:
<223> OTHER INFORMATION: Synthetic

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Met
        35                  40                  45

Gly Arg Ile Asp Pro Glu Asp Gly Glu Thr Lys Tyr Ala Pro Lys Phe
        50                  55                  60

Gln Gly Arg Val Thr Met Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ser Arg Ser Trp Ala Tyr Trp Gly Gln Gly Thr Thr Val Thr Val Ser
            100                 105                 110

Ser

<210> SEQ ID NO 73
<211> LENGTH: 108
<212> TYPE: PRT
<213> ORGANISM: Artificial Sequence
<220> FEATURE:
<223> OTHER INFORMATION: Synthetic

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
        50                  55                  60

Gly Ser Gly Ser Gly Thr Asp Phe Thr Leu Thr Ile Ser Ser Leu Glu
65                  70                  75                  80

-continued

Pro Glu Asp Phe Ala Val Tyr Tyr Cys His Gln Trp Ser Ser Tyr Pro
                85                  90                  95

Arg Thr Phe Gly Gly Gly Thr Lys Val Glu Ile Lys
            100                 105

<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
            35                  40                  45

Ile Tyr Ser Thr Ser Asn Leu Ala Ser Gly Ile Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Ala Ala Val Tyr Phe Cys His Gln Trp Ser Ser Tyr Pro
                85                  90                  95

Arg Thr Phe Gly Gly Gly Thr Lys Val Glu Ile Lys
            100                 105

<210> SEQ ID NO 75
<211> LENGTH: 108
<212> TYPE: PRT
<213> ORGANISM: Artificial Sequence
<220> FEATURE:
<223> OTHER INFORMATION: Synthetic

<400> SEQUENCE: 75

Glu Ile Val Met Thr Gln Ser Pro Pro Thr Leu Ser Leu Ser Pro Gly
1               5                   10                  15

Glu Arg Val Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
            35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys His Gln Trp Ser Ser Tyr Pro
                85                  90                  95

Arg Thr Phe Gly Gly Gly Thr Lys Val Glu Ile Lys
            100                 105

<210> SEQ ID NO 76
<211> LENGTH: 108
<212> TYPE: PRT
<213> ORGANISM: Artificial Sequence
<220> FEATURE:
<223> OTHER INFORMATION: Synthetic -continued

<400> SEQUENCE: 76

Glu Ile Val Met Thr Gln Ser Pro Pro Thr Leu Ser Leu Ser Pro Gly
1               5                   10                  15

Glu Arg Val Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Ala Ala Val Tyr Phe Cys His Gln Trp Ser Ser Tyr Pro
                85                  90                  95

Arg Thr Phe Gly Gly Gly Thr Lys Val Glu Ile Lys
            100                 105

<210> SEQ ID NO 77
<211> LENGTH: 5
<212> TYPE: PRT
<213> ORGANISM: Artificial Sequence
<220> FEATURE:
<223> OTHER INFORMATION: Synthetic

<400> SEQUENCE: 77

Asp Thr Tyr Met His
1               5

<210> SEQ ID NO 78
<211> LENGTH: 17
<212> TYPE: PRT
<213> ORGANISM: Artificial Sequence
<220> FEATURE:
<223> OTHER INFORMATION: Synthetic

<400> SEQUENCE: 78

Arg Ile Asp Pro Ala Asn Val Asn Thr Ile Tyr Asp Pro Lys Phe Gln
1               5                   10                  15

Gly

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Val Gly Ala Tyr Asp Gly Tyr Asp Phe Asp Tyr
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Synthetic

<400> SEQUENCE: 80

Arg Ala Ser Glu Ser Val Asp Asn Tyr Gly Asn Ser Phe Met His
1               5                   10                  15

```
<210> SEQ ID NO 81
<211> LENGTH: 7
<212> TYPE: PRT
<213> ORGANISM: Artificial Sequence
<220> FEATURE:
<223> OTHER INFORMATION: Synthetic

<400> SEQUENCE: 81

Arg Ala Ser Asn Leu Glu Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

Gln Gln Asn Asn Glu Asp Pro Leu Thr
1               5

<210> SEQ ID NO 83
<211> LENGTH: 120
<212> TYPE: PRT
<213> ORGANISM: Artificial Sequence
<220> FEATURE:
<223> OTHER INFORMATION: Synthetic

<400> SEQUENCE: 83

Glu Val Gln Leu Val Gln Ser Gly Ala Glu Val Lys Pro Gly Ala
1               5                   10                  15

Thr Val Lys Ile Ser Cys Lys Val Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Asn Val Asn Thr Ile Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Val Gly Ala Tyr Asp Gly Tyr Asp Phe Asp Tyr Trp Gly Gln
            100                 105                 110

Gly Thr Thr Val Thr Val Ser Ser
        115                 120

<210> SEQ ID NO 84
<211> LENGTH: 120
<212> TYPE: PRT
<213> ORGANISM: Artificial Sequence
<220> FEATURE:
<223> OTHER INFORMATION: Synthetic

<400> SEQUENCE: 84

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45
```

```
Gly Arg Ile Asp Pro Ala Asn Val Asn Thr Ile Tyr Asp Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Val Gly Ala Tyr Asp Gly Tyr Asp Phe Asp Tyr Trp Gly Gln
            100                 105                 110

Gly Thr Thr Val Thr Val Ser Ser
        115                 120
```

```
<210> SEQ ID NO 85
<211> LENGTH: 120
<212> TYPE: PRT
<213> ORGANISM: Artificial Sequence
<220> FEATURE:
<223> OTHER INFORMATION: Synthetic

<400> SEQUENCE: 85
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Val Asn Thr Ile Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Gly Ala Tyr Asp Gly Tyr Asp Phe Asp Tyr Trp Gly Gln
            100                 105                 110

Gly Thr Thr Val Thr Val Ser Ser
        115                 120
```

```
<210> SEQ ID NO 86
<211> LENGTH: 120
<212> TYPE: PRT
<213> ORGANISM: Artificial Sequence
<220> FEATURE:
<223> OTHER INFORMATION: Synthetic

<400> SEQUENCE: 86
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Ala Asn Val Asn Thr Ile Tyr Asp Pro Lys Phe
    50                  55                  60

Gln Gly Arg Val Thr Met Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Val Gly Ala Tyr Asp Gly Tyr Asp Phe Asp Tyr Trp Gly Gln
            100                 105                 110

Gly Thr Thr Val Thr Val Ser Ser
        115                 120

<210> SEQ ID NO 87
<211> LENGTH: 111
<212> TYPE: PRT
<213> ORGANISM: Artificial Sequence
<220> FEATURE:
<223> OTHER INFORMATION: Synthetic

<400> SEQUENCE: 87

Asp Ile Val Met Thr Gln Ser Pro Asp Ser Leu Ala Val Ser Leu Gly
1                   5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Leu Thr Phe Gly Gln Gly Thr Lys Leu Glu Ile Lys
            100                 105                 110

<210> SEQ ID NO 88
<211> LENGTH: 111
<212> TYPE: PRT
<213> ORGANISM: Artificial Sequence
<220> FEATURE:
<223> OTHER INFORMATION: Synthetic

<400> SEQUENCE: 88

Asp Ile Val Leu Thr Gln Ser Pro Asp Ser Leu Ala Val Ser Leu Gly
1                   5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Leu Thr Phe Gly Gln Gly Thr Lys Leu Glu Ile Lys
            100                 105                 110

<210> SEQ ID NO 89
<211> LENGTH: 111
<212> TYPE: PRT
<213> ORGANISM: Artificial Sequence
<220> FEATURE:
<223> OTHER INFORMATION: Synthetic
```

-continued

<400> SEQUENCE: 89

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Asn Ser Phe Met His Trp Tyr Gln Gln Lys Pro Gly Lys Val Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Asn Asn
                85                  90                  95

Glu Asp Pro Leu Thr Phe Gly Gln Gly Thr Lys Leu Glu Ile Lys
            100                 105                 110
```

<210> SEQ ID NO 90
<211> LENGTH: 111
<212> TYPE: PRT
<213> ORGANISM: Artificial Sequence
<220> FEATURE:
<223> OTHER INFORMATION: Synthetic

<400> SEQUENCE: 90

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Asn Ser Phe Met His Trp Tyr Gln Gln Lys Pro Gly Lys Val Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Val Ala Thr Tyr Tyr Cys Gln Gln Asn Asn
                85                  90                  95

Glu Asp Pro Leu Thr Phe Gly Gln Gly Thr Lys Leu Glu Ile Lys
            100                 105                 110
```

<210> SEQ ID NO 91
<211> LENGTH: 5
<212> TYPE: PRT
<213> ORGANISM: Artificial Sequence
<220> FEATURE:
<223> OTHER INFORMATION: Synthetic

<400> SEQUENCE: 91

```
Ser Tyr Val Met His
1               5
```

<210> SEQ ID NO 92
<211> LENGTH: 17
<212> TYPE: PRT
<213> ORGANISM: Artificial Sequence
<220> FEATURE:
<223> OTHER INFORMATION: Synthetic -continued

<400> SEQUENCE: 92

Tyr Ile Asn Pro Tyr Asn Asp Gly Thr Lys Tyr Asn Glu Lys Phe Lys
1               5                   10                  15

Gly

<210> SEQ ID NO 93
<211> LENGTH: 11
<212> TYPE: PRT
<213> ORGANISM: Artificial Sequence
<220> FEATURE:
<223> OTHER INFORMATION: Synthetic

<400> SEQUENCE: 93

Ser Tyr Tyr Asp Tyr Asp Gly Ser Phe Asp Tyr
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic

<400> SEQUENCE: 94

Lys Ala Ser Gln Asp Val Thr Thr Ala Val Ala
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

Ser Ala Ser Tyr Arg Tyr Thr
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln His Tyr Ser Thr Pro Trp Thr
1               5

<210> SEQ ID NO 97
<211> LENGTH: 120
<212> TYPE: PRT
<213> ORGANISM: Artificial Sequence
<220> FEATURE:
<223> OTHER INFORMATION: Synthetic

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Met
            35                  40                  45

-continued

```
Gly Tyr Ile Asn Pro Tyr Asn Asp Gly Thr Lys Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Asp Tyr Asp Gly Ser Phe Asp Tyr Trp Gly Gln
            100                 105                 110

Gly Thr Thr Val Thr Val Ser Ser
        115                 120

<210> SEQ ID NO 98
<211> LENGTH: 120
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Ile Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Asp Tyr Asp Gly Ser Phe Asp Tyr Trp Gly Gln
            100                 105                 110

Gly Thr Thr Val Thr Val Ser Ser
        115                 120

<210> SEQ ID NO 99
<211> LENGTH: 120
<212> TYPE: PRT
<213> ORGANISM: Artificial Sequence
<220> FEATURE:
<223> OTHER INFORMATION: Synthetic

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Asp Tyr Asp Gly Ser Phe Asp Tyr Trp Gly Gln
            100                 105                 110
```

-continued

```
Gly Thr Thr Val Thr Val Ser Ser
        115                 120

<210> SEQ ID NO 100
<211> LENGTH: 120
<212> TYPE: PRT
<213> ORGANISM: Artificial Sequence
<220> FEATURE:
<223> OTHER INFORMATION: Synthetic

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Lys Phe
    50                  55                  60

Lys Gly Arg Val Thr Met Thr Ser Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Tyr Asp Tyr Asp Gly Ser Phe Asp Tyr Trp Gly Gln
            100                 105                 110

Gly Thr Thr Val Thr Val Ser Ser
        115                 120

<210> SEQ ID NO 101
<211> LENGTH: 107
<212> TYPE: PRT
<213> ORGANISM: Artificial Sequence
<220> FEATURE:
<223> OTHER INFORMATION: Synthetic

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 102
<211> LENGTH: 107
<212> TYPE: PRT
<213> ORGANISM: Artificial Sequence
<220> FEATURE:
<223> OTHER INFORMATION: Synthetic
```

-continued

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Thr Ala
            20                  25                  30

Val Ala Trp Tyr Gln Gln Lys Pro Gly Lys Val Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 103
<211> LENGTH: 5
<212> TYPE: PRT
<213> ORGANISM: Artificial Sequence
<220> FEATURE:
<223> OTHER INFORMATION: Synthetic

<400> SEQUENCE: 103

Asp Thr Tyr Ile His
1               5

<210> SEQ ID NO 104
<211> LENGTH: 17
<212> TYPE: PRT
<213> ORGANISM: Artificial Sequence
<220> FEATURE:
<223> OTHER INFORMATION: Synthetic

<400> SEQUENCE: 104

Arg Ile Asp Pro Ala Asp Gly Asp Thr Lys His Asn Pro Lys Phe His
1               5                   10                  15

Asp

<210> SEQ ID NO 105
<211> LENGTH: 5
<212> TYPE: PRT
<213> ORGANISM: Artificial Sequence
<220> FEATURE:
<223> OTHER INFORMATION: Synthetic

<400> SEQUENCE: 105

Gly Asn Tyr Val Asn
1               5

<210> SEQ ID NO 106
<211> LENGTH: 12
<212> TYPE: PRT
<213> ORGANISM: Artificial Sequence
<220> FEATURE:
<223> OTHER INFORMATION: Synthetic

<400> SEQUENCE: 106

Arg Ala Ser Ser Ser Val Thr Ser Ser Tyr Leu Tyr
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Synthetic

<400> SEQUENCE: 107

Ser Ala Ser Asn Leu Ala Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

His Gln Trp Tyr Ser Tyr Pro Arg Thr
1               5

<210> SEQ ID NO 109
<211> LENGTH: 114
<212> TYPE: PRT
<213> ORGANISM: Artificial Sequence
<220> FEATURE:
<223> OTHER INFORMATION: Synthetic

<400> SEQUENCE: 109

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Phe Glu Asp Thr
            20                  25                  30

Tyr Ile His Trp Val Gln Gln Ala Pro Gly Lys Gly Leu Glu Trp Met
        35                  40                  45

Gly Arg Ile Asp Pro Ala Asp Gly Asp Thr Lys His Asn Pro Lys Phe
    50                  55                  60

His Asp Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Asn Tyr Val Asn Trp Gly Gln Gly Thr Thr Val Thr Val
            100                 105                 110

Ser Ser

<210> SEQ ID NO 110
<211> LENGTH: 114
<212> TYPE: PRT
<213> ORGANISM: Artificial Sequence
<220> FEATURE:
<223> OTHER INFORMATION: Synthetic

<400> SEQUENCE: 110

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Phe Glu Asp Thr
            20                  25                  30

Tyr Ile His Trp Val Gln Gln Ala Pro Gly Lys Gly Leu Glu Trp Met
        35                  40                  45

Gly Arg Ile Asp Pro Ala Asp Gly Asp Thr Lys His Asn Pro Lys Phe
    50                  55                  60

```
His Asp Arg Val Thr Ile Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Asn Tyr Val Asn Trp Gly Gln Gly Thr Thr Val Thr Val
            100                 105                 110

Ser Ser

<210> SEQ ID NO 111
<211> LENGTH: 114
<212> TYPE: PRT
<213> ORGANISM: Artificial Sequence
<220> FEATURE:
<223> OTHER INFORMATION: Synthetic

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Glu Asp Thr
                20                  25                  30

Tyr Ile His Trp Val Arg Gln Ala Pro Gly Gln Gly Leu Glu Trp Met
        35                  40                  45

Gly Arg Ile Asp Pro Ala Asp Gly Asp Thr Lys His Asn Pro Lys Phe
    50                  55                  60

His Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Tyr Val Asn Trp Gly Gln Gly Thr Thr Val Thr Val
            100                 105                 110

Ser Ser

<210> SEQ ID NO 112
<211> LENGTH: 114
<212> TYPE: PRT
<213> ORGANISM: Artificial Sequence
<220> FEATURE:
<223> OTHER INFORMATION: Synthetic

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Phe Glu Asp Thr
                20                  25                  30

Tyr Ile His Trp Val Arg Gln Ala Pro Gly Gln Gly Leu Glu Trp Met
        35                  40                  45

Gly Arg Ile Asp Pro Ala Asp Gly Asp Thr Lys His Asn Pro Lys Phe
    50                  55                  60

His Asp Arg Val Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Val Arg Gly Asn Tyr Val Asn Trp Gly Gln Gly Thr Thr Val Thr Val
            100                 105                 110

Ser Ser
```

<210> SEQ ID NO 113
<211> LENGTH: 108
<212> TYPE: PRT
<213> ORGANISM: Artificial Sequence
<220> FEATURE:
<223> OTHER INFORMATION: Synthetic

<400> SEQUENCE: 113

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Ser Ser
            20                  25                  30

Tyr Leu Tyr Trp Tyr Gln Gln Lys Pro Gly Gln Ala Pro Arg Leu Leu
        35                  40                  45

Ile Tyr Ser Ala Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Tyr Ser Tyr Pro
                85                  90                  95

Arg Thr Phe Gly Gly Gly Thr Lys Val Glu Ile Lys
            100                 105

<210> SEQ ID NO 114
<211> LENGTH: 108
<212> TYPE: PRT
<213> ORGANISM: Artificial Sequence
<220> FEATURE:
<223> OTHER INFORMATION: Synthetic

<400> SEQUENCE: 114

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Thr Ser Ser
            20                  25                  30

Tyr Leu Tyr Trp Tyr Gln Gln Lys Pro Gly Gln Ala Pro Arg Leu Leu
        35                  40                  45

Ile Tyr Ser Ala Ser Asn Leu Ala Ser Gly Ile Pro Ala Arg Phe Ser
    50                  55                  60

Gly Ser Gly Ser Gly Thr Asp Tyr Thr Leu Thr Ile Ser Ser Leu Glu
65                  70                  75                  80

Pro Glu Asp Ala Ala Val Tyr Phe Cys His Gln Trp Tyr Ser Tyr Pro
                85                  90                  95

Arg Thr Phe Gly Gly Gly Thr Lys Val Glu Ile Lys
            100                 105

<210> SEQ ID NO 115
<211> LENGTH: 108
<212> TYPE: PRT
<213> ORGANISM: Artificial Sequence
<220> FEATURE:
<223> OTHER INFORMATION: Synthetic

<400> SEQUENCE: 115

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Thr Ser Ser
            20                  25                  30

Tyr Leu Tyr Trp Tyr Gln Gln Lys Pro Gly Gln Ala Pro Arg Leu Leu
        35                  40                  45

-continued

```
Ile Tyr Ser Ala Ser Asn Leu Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Trp Tyr Ser Tyr Pro
                85                  90                  95

Arg Thr Phe Gly Gly Gly Thr Lys Val Glu Ile Lys
            100                 105

<210> SEQ ID NO 116
<211> LENGTH: 108
<212> TYPE: PRT
<213> ORGANISM: Artificial Sequence
<220> FEATURE:
<223> OTHER INFORMATION: Synthetic

<400> SEQUENCE: 116

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Thr Ser Ser
                20                  25                  30

Tyr Leu Tyr Trp Tyr Gln Gln Lys Pro Gly Gln Ala Pro Arg Leu Leu
            35                  40                  45

Ile Tyr Ser Ala Ser Asn Leu Ala Ser Gly Ile Pro Asp Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Ala Ala Val Tyr Phe Cys His Gln Trp Tyr Ser Tyr Pro
                85                  90                  95

Arg Thr Phe Gly Gly Gly Thr Lys Val Glu Ile Lys
            100                 105

<210> SEQ ID NO 117
<211> LENGTH: 108
<212> TYPE: PRT
<213> ORGANISM: Artificial Sequence
<220> FEATURE:
<223> OTHER INFORMATION: Synthetic

<400> SEQUENCE: 117

Glu Ile Val Met Thr Gln Ser Pro Pro Thr Leu Ser Leu Ser Pro Gly
1               5                   10                  15

Glu Arg Val Thr Leu Ser Cys Arg Ala Ser Ser Ser Val Thr Ser Ser
                20                  25                  30

Tyr Leu Tyr Trp Tyr Gln Gln Lys Pro Gly Gln Ala Pro Arg Leu Leu
            35                  40                  45

Ile Tyr Ser Ala Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys His Gln Trp Tyr Ser Tyr Pro
                85                  90                  95

Arg Thr Phe Gly Gly Gly Thr Lys Val Glu Ile Lys
            100                 105

<210> SEQ ID NO 118
<211> LENGTH: 108
<212> TYPE: PRT
```

```
<213> ORGANISM: Artificial Sequence
<220> FEATURE:
<223> OTHER INFORMATION: Synthetic

<400> SEQUENCE: 118

Glu Ile Val Met Thr Gln Ser Pro Pro Thr Leu Ser Leu Ser Pro Gly
1               5                   10                  15

Glu Arg Val Thr Leu Ser Cys Arg Ala Ser Ser Ser Val Thr Ser Ser
                20                  25                  30

Tyr Leu Tyr Trp Tyr Gln Gln Lys Pro Gly Gln Ala Pro Arg Leu Leu
            35                  40                  45

Ile Tyr Ser Ala Ser Asn Leu Ala Ser Gly Ile Pro Ala Arg Phe Ser
        50                  55                  60

Gly Ser Gly Ser Gly Thr Asp Tyr Thr Leu Thr Ile Ser Ser Leu Gln
65                  70                  75                  80

Pro Glu Asp Ala Ala Val Tyr Phe Cys His Gln Trp Tyr Ser Tyr Pro
                85                  90                  95

Arg Thr Phe Gly Gly Gly Thr Lys Val Glu Ile Lys
            100                 105
```

ANTI-SIRPα MONOCLONAL ANTIBODIES AND USES THEREOF

CROSS REFERENCE TO RELATED APPLICATIONS

The present application is a continuation of International Application No. PCT/CN2020/138800, filed Dec. 24, 2020, which claims priority to PCT/CN2019/127915, filed Dec. 24, 2019, the contents of each of which is incorporated herein by reference in its entirety in the present disclosure.

SEQUENCE LISTING

The instant application contains a Sequence Listing which has been submitted in ASCII format via EFS-Web and is hereby incorporated by reference in its entirety. Said ASCII copy, created on Feb. 11, 2022, is named Sequences.txt and is 84,352 bytes in size.

BACKGROUND

Signal regulatory protein alpha (SIRPα) is a member of the signal-regulatory-protein (SIRP) family, and also belongs to the immunoglobulin superfamily. SIRP family members are receptor-type transmembrane glycoproteins known to be involved in the negative regulation of receptor tyrosine kinase-coupled signaling processes. SIRPα can be phosphorylated by tyrosine kinases. The phospho-tyrosine residues of this PTP have been shown to recruit SH2 domain containing tyrosine phosphatases (PTP), and serve as substrates of PTPs. SIRPα was found to participate in signal transduction mediated by various growth factor receptors. CD47 has been demonstrated to be a ligand. SIRPα shares very high similarity with several other members of the SIRP family. SIRPα is expressed mainly by myeloid cells and also by stem cells or neurons.

SIRPα acts as inhibitory receptor and interacts with a broadly expressed transmembrane protein CD47 also called the "don't eat me" signal. This interaction negatively controls effector function of innate immune cells such as host cell phagocytosis. SIRPα diffuses laterally on the macrophage membrane and accumulates at a phagocytic synapse to bind CD47 and signal 'self', which inhibits the cytoskeleton-intensive process of phagocytosis by the macrophage.

Upon CD47 ligation, SIRPα is phosphorylated and recruits phosphatases like SHP1 and SHP2. The extracellular region contains three Immunoglobulin superfamily domains—single V-set and two C1-set IgSF domains. SIRP β and γ have the similar extracellular structure but different cytoplasmic regions giving contrasting types of signals.

SIRPα recognizes CD47, an anti-phagocytic signal that distinguishes live cells from dying cells. The extracellular domain of SIRPα binds to CD47 and transmits intracellular signals through its cytoplasmic domain. CD47-binding is mediated through the NH2-terminal V-like domain of SIRPα. The cytoplasmic region contains four ITIMs that become phosphorylated after binding of ligand. The phosphorylation mediates activation of tyrosine kinase SHP2. SIRPα also binds phosphatase SHP1, adaptor protein SCAP2 and FYN-binding protein. Recruitment of SHP phosphatases to the membrane leads to the inhibition of myosin accumulation at the cell surface and results in the inhibition of phagocytosis.

Cancer cells highly express CD47 that activates SIRPα and inhibits macrophage-mediated destruction. It has been shown that high-affinity variants of SIRPα that antagonized CD47 on cancer cells increased phagocytosis of cancer cells. Anti-SIRPα antibodies have also been shown to help macrophages to reduce cancer growth and metastasis, alone and in synergy with other cancer treatments.

SUMMARY

Anti-SIRPα antibodies are discovered herein that have high affinity to both variants v1 and v2, can dose-dependently and efficiently block the interaction between SIRPα and CD47, and effectively induce macrophage mediated phagocytosis of cells expressing CD47. By contrast, known anti-SIRPα antibodies can only recognize variant 1.

In accordance with one embodiment of the present disclosure, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein (a) the CDRH1 comprises the amino acid sequence of SEQ ID NO: 15, the CDRH2 comprises the amino acid sequence of SEQ ID NO: 16, 21 or 22, the CDRH3 comprises the amino acid sequence of SEQ ID NO: 17, the CDRL1 comprises the amino acid sequence of SEQ ID NO: 18, the CDRL2 comprises the amino acid sequence of SEQ ID NO: 19, and the CDRL3 comprises the amino acid sequence of SEQ ID NO: 20; (b) the CDRH1 comprises the amino acid sequence of SEQ ID NO: 30, the CDRH2 comprises the amino acid sequence of SEQ ID NO: 31, 36, 37 or 38, the CDRH3 comprises the amino acid sequence of SEQ ID NO: 32, the CDRL1 comprises the amino acid sequence of SEQ ID NO: 33, the CDRL2 comprises the amino acid sequence of SEQ ID NO: 34, and the CDRL3 comprises the amino acid sequence of SEQ ID NO: 35; (c) the CDRH1 comprises the amino acid sequence of SEQ ID NO: 47, the CDRH2 comprises the amino acid sequence of SEQ ID NO: 48, 53 or 54, the CDRH3 comprises the amino acid sequence of SEQ ID NO: 49, the CDRL1 comprises the amino acid sequence of SEQ ID NO: 50, the CDRL2 comprises the amino acid sequence of SEQ ID NO: 51, and the CDRL3 comprises the amino acid sequence of SEQ ID NO: 52; (d) the CDRH1 comprises the amino acid sequence of SEQ ID NO: 63, the CDRH2 comprises the amino acid sequence of SEQ ID NO: 64, the CDRH3 comprises the amino acid sequence of SEQ ID NO: 65, the CDRL1 comprises the amino acid sequence of SEQ ID NO: 66, the CDRL2 comprises the amino acid sequence of SEQ ID NO: 67, and the CDRL3 comprises the amino acid sequence of SEQ ID NO: 68; (e) the CDRH1 comprises the amino acid sequence of SEQ ID NO: 77, the CDRH2 comprises the amino acid sequence of SEQ ID NO: 78, the CDRH3 comprises the amino acid sequence of SEQ ID NO: 79, the CDRL1 comprises the amino acid sequence of SEQ ID NO: 80, the CDRL2 comprises the amino acid sequence of SEQ ID NO: 81, and the CDRL3 comprises the amino acid sequence of SEQ ID NO: 82; (f) the CDRH1 comprises the amino acid sequence of SEQ ID NO: 91, the CDRH2 comprises the amino acid sequence of SEQ ID NO: 92, the CDRH3 comprises the amino acid sequence of SEQ ID NO: 93, the CDRL1 comprises the amino acid sequence of SEQ ID NO: 94, the CDRL2 comprises the amino acid sequence of SEQ ID NO: 95, and the CDRL3 comprises the amino acid sequence of SEQ ID NO: 96; or (g) the CDRH1 comprises the amino acid sequence of SEQ ID NO: 103, the CDRH2 comprises the amino acid sequence of SEQ ID NO: 104, the CDRH3 comprises the amino acid sequence of SEQ ID NO: 105, the CDRL1 comprises the amino acid sequence of SEQ ID NO: 106, the CDRL2 comprises the amino acid sequence of SEQ ID NO: 107, and the CDRL3 comprises the amino acid sequence of SEQ ID NO: 108.

In one embodiment, the present disclosure provides an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 15, the CDRH2 comprises the amino acid sequence of SEQ ID NO: 16, 21 or 22, the CDRH3 comprises the amino acid sequence of SEQ ID NO: 17, the CDRL1 comprises the amino acid sequence of SEQ ID NO: 18, the CDRL2 comprises the amino acid sequence of SEQ ID NO: 19, and the CDRL3 comprises the amino acid sequence of SEQ ID NO: 20.

In some embodiments, the heavy chain variable region comprises an amino acid sequence selected from the group consisting of SEQ ID NO:1 and 23-27, or a peptide having at least 90% sequence identity to an amino acid sequence selected from the group consisting of SEQ ID NO:1 and 23-27.

In some embodiments, the light chain variable region comprises an amino acid sequence selected from the group consisting of SEQ ID NO:2 and 28-29, or a peptide having at least 90% sequence identity to an amino acid sequence selected from the group consisting of SEQ ID NO:2 and 28-29.

In some embodiments, the heavy chain variable region comprises the amino acid sequence of SEQ ID NO:27 and the light chain variable region comprises the amino acid sequence of SEQ ID NO:29.

In another embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 30, the CDRH2 comprises the amino acid sequence of SEQ ID NO: 31, 36, 37 or 38, the CDRH3 comprises the amino acid sequence of SEQ ID NO: 32, the CDRL1 comprises the amino acid sequence of SEQ ID NO: 33, the CDRL2 comprises the amino acid sequence of SEQ ID NO: 34, and the CDRL3 comprises the amino acid sequence of SEQ ID NO: 35.

In some embodiments, the heavy chain variable region comprises an amino acid sequence selected from the group consisting of SEQ ID NO:3 and 39-44, or a peptide having at least 90% sequence identity to an amino acid sequence selected from the group consisting of SEQ ID NO:3 and 39-44.

In some embodiments, the light chain variable region comprises an amino acid sequence selected from the group consisting of SEQ ID NO:4 and 45-46, or a peptide having at least 90% sequence identity to an amino acid sequence selected from the group consisting of SEQ ID NO:4 and 45-46.

In some embodiments, the heavy chain variable region comprises the amino acid sequence of SEQ ID NO:43 and the light chain variable region comprises the amino acid sequence of SEQ ID NO:45.

Yet another embodiment provides an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 47, the CDRH2 comprises the amino acid sequence of SEQ ID NO: 48, 53 or 54, the CDRH3 comprises the amino acid sequence of SEQ ID NO: 49, the CDRL1 comprises the amino acid sequence of SEQ ID NO: 50, the CDRL2 comprises the amino acid sequence of SEQ ID NO: 51, and the CDRL3 comprises the amino acid sequence of SEQ ID NO: 52;

In some embodiments, the heavy chain variable region comprises an amino acid sequence selected from the group consisting of SEQ ID NO:5 and 55-60, or a peptide having at least 90% sequence identity to an amino acid sequence selected from the group consisting of SEQ ID NO:5 and 55-60.

In some embodiments, the light chain variable region comprises an amino acid sequence selected from the group consisting of SEQ ID NO:6 and 61-62, or a peptide having at least 90% sequence identity to an amino acid sequence selected from the group consisting of SEQ ID NO: 6 and 61-62.

In some embodiments, the presently disclosed antibody or fragment can bind to SIRPα variant 1 and variant 2. In some embodiments, the antibody or fragment is humanized. In some embodiments, the presently disclosed antibody or fragment further has a binding specificity to a second target protein.

Also provided, in some embodiments, are compositions comprising the antibody or fragment thereof and a pharmaceutically acceptable carrier. In some embodiments, the composition further comprises a second antibody having specificity to a tumor antigen. In some embodiments, the second antibody is a tumor-opsonizing antibody.

Methods and uses for the treatment of diseases and conditions are also provided. In one embodiment, provided is a method of treating cancer in a patient in need thereof, comprising administering to the patient the antibody or fragment thereof of the present disclosure.

DETAILED DESCRIPTION

Definitions

Figure 1:
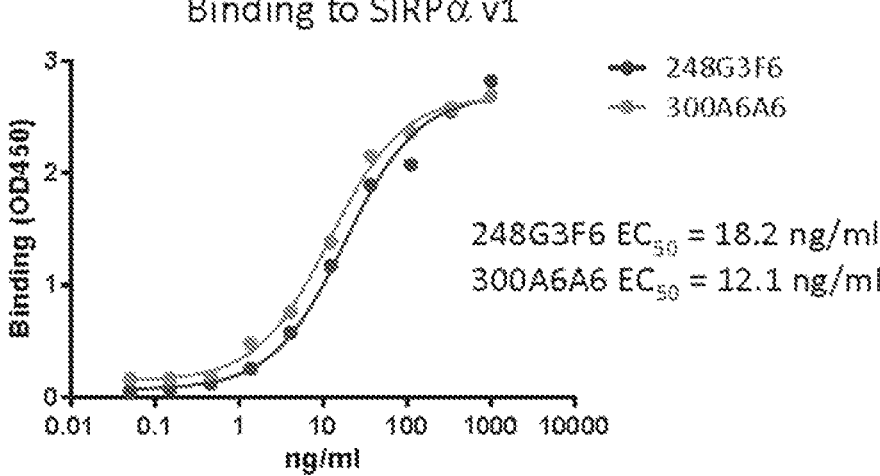
FIG. 1 shows cross-binding to SIRPα v1 and v2 by the antibodies.
Figure 1:
Figure 1:
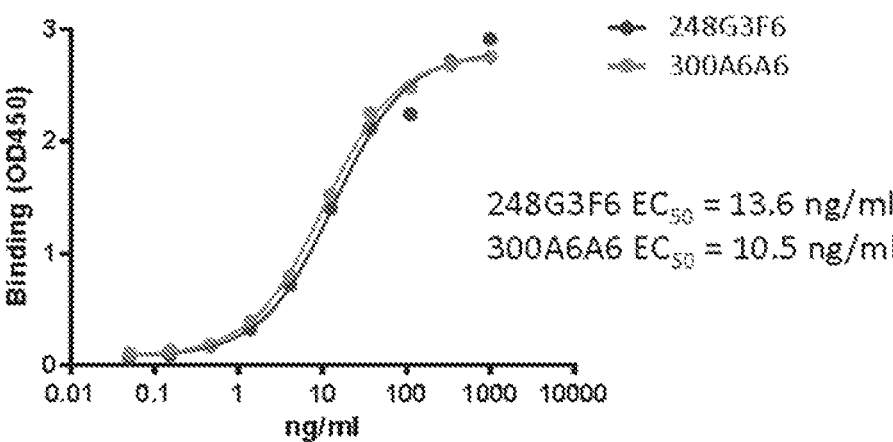

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\varepsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and

7

8

F(ab')₂, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, λ). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.*, 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

|  | Kabat | Chothia |
|---|---|---|
| CDR-H1 | 31-35 | 26-32 |
| CDR-H2 | 50-65 | 52-58 |
| CDR-H3 | 95-102 | 95-102 |
| CDR-L1 | 24-34 | 26-32 |
| CDR-L2 | 50-56 | 50-52 |
| CDR-L3 | 89-97 | 91-96 |

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983).

In addition to table above, the Kabat number system describes the CDR regions as follows: CDR-H1 begins at approximately amino acid 31 (i.e., approximately 9 residues after the first cysteine residue), includes approximately 5-7 amino acids, and ends at the next tryptophan residue. CDR-H2 begins at the fifteenth residue after the end of CDR-H1, includes approximately 16-19 amino acids, and ends at the next arginine or lysine residue. CDR-H3 begins at approximately the thirty third amino acid residue after the end of CDR-H2; includes 3-25 amino acids; and ends at the sequence W-G-X-G, where X is any amino acid. CDR-L1 begins at approximately residue 24 (i.e., following a cysteine residue); includes approximately 10-17 residues; and ends at the next tryptophan residue. CDR-L2 begins at approximately the sixteenth residue after the end of CDR-L1 and includes approximately 7 residues. CDR-L3 begins at approximately the thirty third residue after the end of CDR-L2 (i.e., following a cysteine residue); includes approximately 7-11 residues and ends at the sequence F or W-G-X-G, where X is any amino acid.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an IgG$_1$ molecule and a hinge region derived from an IgG$_3$ molecule. In another example, a heavy chain constant region can comprise a hinge region derived, in part, from an IgG$_1$ molecule and, in part, from an IgG$_3$ molecule. In another example, a heavy chain portion can comprise a chimeric hinge derived, in part, from an IgG$_1$ molecule and, in part, from an IgG$_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain.

The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

As used herein, "percent humanization" is calculated by determining the number of framework amino acid differences (i.e., non-CDR difference) between the humanized domain and the germline domain, subtracting that number from the total number of amino acids, and then dividing that by the total number of amino acids and multiplying by 100.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-SIRPα Antibodies

The present disclosure provides anti-SIRPα antibodies and fragments that have high affinity to both variants v1 and v2. Variant 1 (hSIRPαV1) is the dominant variant among Europeans, Africans, Ad mixed Americans, and South Asians. Variant 2 (hSIRPαV2) is the dominant variant among East Asians. Sequences of hSIRPαV1 and hSIRPαV2 differ within the extracellular Ig-like V-like (IgV) domain. The ability of the instantly disclosed antibodies and fragments to recognize both variants enables them to be effective among the widest patient population.

Moreover, the instant antibodies and fragments exhibited excellent binding affinity, potent induction of macrophage-mediated phagocytosis, and superior chemistry, manufacturing, and control (CMC) developability.

In accordance with one embodiment of the present disclosure, therefore, provided are antibodies and antigen-binding fragments thereof that are able to bind to both variants 1 and 2 of SIRPα. Example antibodies include those murine ones listed in Table 1, as well as humanized ones of Tables 2-8. Also included are those that include the same CDRs as illustrated herein. In some embodiments, the disclosed antibodies and fragments include those that bind to the same epitope as those illustrated here, and those that compete with the instantly disclosed in binding to SIRPα.

In accordance with one embodiment of the present disclosure, provided is an antibody or fragment thereof that includes the heavy chain and light chain variable domains with the CDR regions disclosed herein, as well as their biological equivalents.

In one embodiment, the CDRs are those of 248G3F6, as exemplified in Tables 2B and 2D. In one embodiment, the CDRH1 comprises the amino acid sequence of SEQ ID NO: 15 or a variant thereof having one, two, or three deletions, additions, substitutions or the combinations thereof, the CDRH2 comprises the amino acid sequence of SEQ ID NO: 16, 21 or 22 or a variant thereof having one, two, or three deletions, additions, substitutions or the combinations thereof, the CDRH3 comprises the amino acid sequence of SEQ ID NO: 17 or a variant thereof having one, two, or three deletions, additions, substitutions or the combinations thereof, the CDRL1 comprises the amino acid sequence of SEQ ID NO: 18 or a variant thereof having one, two, or three deletions, additions, substitutions or the combinations thereof, the CDRL2 comprises the amino acid sequence of SEQ ID NO: 19 or a variant thereof having one, two, or three deletions, additions, substitutions or the combinations thereof, and the CDRL3 comprises the amino acid sequence of SEQ ID NO: 20 or a variant thereof having one, two, or three deletions, additions, substitutions or the combinations thereof.

One embodiment provides an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 15, the CDRH2 comprises the amino acid sequence of SEQ ID NO: 16, the CDRH3 comprises the amino acid sequence of SEQ ID NO: 17, the CDRL1 comprises the amino acid sequence of SEQ ID NO: 18, the CDRL2 comprises the amino acid sequence of SEQ ID NO: 19, and the CDRL3 comprises the amino acid sequence of SEQ ID NO: 20.

One embodiment provides an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 15, the CDRH2 comprises the amino acid sequence of SEQ ID NO: 21, the CDRH3 comprises the amino acid sequence of SEQ ID NO: 17, the CDRL1 comprises the amino acid sequence of SEQ ID NO: 18, the CDRL2 comprises the amino acid sequence of SEQ ID NO: 19, and the CDRL3 comprises the amino acid sequence of SEQ ID NO: 20.

One embodiment provides an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 15, the CDRH2 comprises the amino acid sequence of SEQ ID NO: 22, the CDRH3 comprises the amino acid sequence of SEQ ID NO: 17, the CDRL1 comprises the amino acid sequence of SEQ ID NO: 18, the CDRL2 comprises the amino acid sequence of SEQ ID NO: 19, and the CDRL3 comprises the amino acid sequence of SEQ ID NO: 20.

In some embodiments, the heavy chain variable region comprises an amino acid sequence selected from the group consisting of SEQ ID NO:1 and 23-27, or a peptide having at least 90% sequence identity to an amino acid sequence selected from the group consisting of SEQ ID NO:1 and 23-27.

In some embodiments, the light chain variable region comprises an amino acid sequence selected from the group consisting of SEQ ID NO:2 and 28-29, or a peptide having at least 90% sequence identity to an amino acid sequence selected from the group consisting of SEQ ID NO:2 and 28-29.

In some embodiments, the heavy chain variable region comprises the amino acid sequence of SEQ ID NO:27 and the light chain variable region comprises the amino acid sequence of SEQ ID NO:29.

In one embodiment, the CDRs are those of 300A6A6, as exemplified in Tables 3B and 3D. In one embodiment, the CDRH1 comprises the amino acid sequence of SEQ ID NO: 30 or a variant thereof having one, two, or three deletions, additions, substitutions or the combinations thereof, the CDRH2 comprises the amino acid sequence of SEQ ID NO: 31, 36, 37 or 38 or a variant thereof having one, two, or three deletions, additions, substitutions or the combinations thereof, the CDRH3 comprises the amino acid sequence of SEQ ID NO: 32 or a variant thereof having one, two, or three deletions, additions, substitutions or the combinations thereof, the CDRL1 comprises the amino acid sequence of SEQ ID NO: 33 or a variant thereof having one, two, or three deletions, additions, substitutions or the combinations thereof, the CDRL2 comprises the amino acid sequence of SEQ ID NO: 34 or a variant thereof having one, two, or three deletions, additions, substitutions or the combinations thereof, and the CDRL3 comprises the amino acid sequence of SEQ ID NO: 35 or a variant thereof having one, two, or three deletions, additions, substitutions or the combinations thereof.

In one embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 30, the CDRH2 comprises the amino acid sequence of SEQ ID NO: 31, the CDRH3 comprises the amino acid sequence of SEQ ID NO: 32, the CDRL1 comprises the amino acid sequence of SEQ ID NO: 33, the CDRL2 comprises the amino acid sequence of SEQ ID NO: 34, and the CDRL3 comprises the amino acid sequence of SEQ ID NO: 35.

In one embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 30, the CDRH2 comprises the amino acid sequence of SEQ ID NO: 36, the CDRH3 comprises the amino acid sequence of SEQ ID NO: 32, the CDRL1 comprises the amino acid sequence of SEQ ID NO: 33, the CDRL2 comprises the amino acid sequence of SEQ ID NO: 34, and the CDRL3 comprises the amino acid sequence of SEQ ID NO: 35.

In one embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 30, the CDRH2 comprises the amino acid sequence of SEQ ID NO: 37, the CDRH3 comprises the amino acid sequence of SEQ ID NO: 32, the CDRL1 comprises the amino acid sequence of SEQ ID NO: 33, the CDRL2 comprises the amino acid sequence of SEQ ID NO: 34, and the CDRL3 comprises the amino acid sequence of SEQ ID NO: 35.

In one embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 30, the CDRH2 comprises the amino acid sequence of SEQ ID NO: 38, the CDRH3 comprises the amino acid sequence of SEQ ID NO: 32, the CDRL1 comprises the amino acid sequence of SEQ ID NO: 33, the CDRL2 comprises the amino acid sequence of SEQ ID NO: 34, and the CDRL3 comprises the amino acid sequence of SEQ ID NO: 35.

In some embodiments, the heavy chain variable region comprises an amino acid sequence selected from the group consisting of SEQ ID NO:3 and 39-44, or a peptide having at least 90% sequence identity to an amino acid sequence selected from the group consisting of SEQ ID NO:3 and 39-44.

In some embodiments, the light chain variable region comprises an amino acid sequence selected from the group consisting of SEQ ID NO:4 and 45-46, or a peptide having at least 90% sequence identity to an amino acid sequence selected from the group consisting of SEQ ID NO:4 and 45-46.

In some embodiments, the heavy chain variable region comprises the amino acid sequence of SEQ ID NO:43 and the light chain variable region comprises the amino acid sequence of SEQ ID NO:45.

In one embodiment, the CDRs are those of 102A10F2, as exemplified in Tables 4B and 4D. In one embodiment, the CDRH1 comprises the amino acid sequence of SEQ ID NO: 47 or a variant thereof having one, two, or three deletions, additions, substitutions or the combinations thereof, the CDRH2 comprises the amino acid sequence of SEQ ID NO: 48, 53 or 54 or a variant thereof having one, two, or three deletions, additions, substitutions or the combinations thereof, the CDRH3 comprises the amino acid sequence of SEQ ID NO: 49 or a variant thereof having one, two, or three deletions, additions, substitutions or the combinations thereof, the CDRL1 comprises the amino acid sequence of SEQ ID NO: 50 or a variant thereof having one, two, or three deletions, additions, substitutions or the combinations thereof, the CDRL2 comprises the amino acid sequence of SEQ ID NO: 51 or a variant thereof having one, two, or three deletions, additions, substitutions or the combinations thereof, and the CDRL3 comprises the amino acid sequence of SEQ ID NO: 52 or a variant thereof having one, two, or three deletions, additions, substitutions or the combinations thereof.

In one embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 47, the CDRH2 comprises the amino acid sequence of SEQ ID NO: 48, the CDRH3 comprises the amino acid sequence of SEQ ID NO: 49, the CDRL1 comprises the amino acid sequence of SEQ ID NO: 50, the CDRL2 comprises the amino acid sequence of SEQ ID NO: 51, and the CDRL3 comprises the amino acid sequence of SEQ ID NO: 52.

In one embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 47, the CDRH2 comprises the amino acid sequence of SEQ ID NO: 53, the CDRH3 comprises the amino acid sequence of SEQ ID NO: 49, the CDRL1 comprises the amino acid sequence of SEQ ID NO: 50, the CDRL2 comprises the amino acid sequence of SEQ ID NO: 51, and the CDRL3 comprises the amino acid sequence of SEQ ID NO: 52.

In one embodiment, provided is an antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 47, the CDRH2 comprises the amino acid sequence of SEQ ID NO: 54, the CDRH3 comprises the amino acid sequence of SEQ ID NO: 49, the CDRL1 comprises the amino acid sequence of SEQ ID NO: 50, the CDRL2 comprises the amino acid sequence of SEQ ID NO: 51, and the CDRL3 comprises the amino acid sequence of SEQ ID NO: 52.

In some embodiments, the heavy chain variable region comprises an amino acid sequence selected from the group consisting of SEQ ID NO:5 and 55-60, or a peptide having at least 90% sequence identity to an amino acid sequence selected from the group consisting of SEQ ID NO:5 and 55-60.

In some embodiments, the light chain variable region comprises an amino acid sequence selected from the group consisting of SEQ ID NO:6 and 61-62, or a peptide having at least 90% sequence identity to an amino acid sequence selected from the group consisting of SEQ ID NO: 6 and 61-62.

In one embodiment, the CDRs are those of 62D2H6, as exemplified in Tables 5B and 5D. In one embodiment, the CDRH1 comprises the amino acid sequence of SEQ ID NO: 63 or a variant thereof having one, two, or three deletions, additions, substitutions or the combinations thereof, the CDRH2 comprises the amino acid sequence of SEQ ID NO: 64 or a variant thereof having one, two, or three deletions, additions, substitutions or the combinations thereof, the CDRH3 comprises the amino acid sequence of SEQ ID NO: 65 or a variant thereof having one, two, or three deletions, additions, substitutions or the combinations thereof, the CDRL1 comprises the amino acid sequence of SEQ ID NO:

66 or a variant thereof having one, two, or three deletions, additions, substitutions or the combinations thereof, the CDRL2 comprises the amino acid sequence of SEQ ID NO: 67 or a variant thereof having one, two, or three deletions, additions, substitutions or the combinations thereof, and the CDRL3 comprises the amino acid sequence of SEQ ID NO: 68 or a variant thereof having one, two, or three deletions, additions, substitutions or the combinations thereof.

In some embodiments, the heavy chain variable region comprises an amino acid sequence selected from the group consisting of SEQ ID NO:7 and 69-72, or a peptide having at least 90% sequence identity to an amino acid sequence selected from the group consisting of SEQ ID NO:7 and 69-72.

In some embodiments, the light chain variable region comprises an amino acid sequence selected from the group consisting of SEQ ID NO:8 and 73-76, or a peptide having at least 90% sequence identity to an amino acid sequence selected from the group consisting of SEQ ID NO: 8 and 73-76.

In one embodiment, the CDRs are those of 211F8E11, as exemplified in Tables 6B and 6D. In one embodiment, the CDRH1 comprises the amino acid sequence of SEQ ID NO: 77 or a variant thereof having one, two, or three deletions, additions, substitutions or the combinations thereof, the CDRH2 comprises the amino acid sequence of SEQ ID NO: 78 or a variant thereof having one, two, or three deletions, additions, substitutions or the combinations thereof, the CDRH3 comprises the amino acid sequence of SEQ ID NO: 79 or a variant thereof having one, two, or three deletions, additions, substitutions or the combinations thereof, the CDRL1 comprises the amino acid sequence of SEQ ID NO: 80 or a variant thereof having one, two, or three deletions, additions, substitutions or the combinations thereof, the CDRL2 comprises the amino acid sequence of SEQ ID NO: 81 or a variant thereof having one, two, or three deletions, additions, substitutions or the combinations thereof, and the CDRL3 comprises the amino acid sequence of SEQ ID NO: 82 or a variant thereof having one, two, or three deletions, additions, substitutions or the combinations thereof.

In some embodiments, the heavy chain variable region comprises an amino acid sequence selected from the group consisting of SEQ ID NO:9 and 83-86, or a peptide having at least 90% sequence identity to an amino acid sequence selected from the group consisting of SEQ ID NO:9 and 83-86.

In some embodiments, the light chain variable region comprises an amino acid sequence selected from the group consisting of SEQ ID NO:10 and 87-90, or a peptide having at least 90% sequence identity to an amino acid sequence selected from the group consisting of SEQ ID NO: 10 and 87-90.

In one embodiment, the CDRs are those of 217D11E5, as exemplified in Tables 7B and 7D. In one embodiment, the CDRH1 comprises the amino acid sequence of SEQ ID NO: 91 or a variant thereof having one, two, or three deletions, additions, substitutions or the combinations thereof, the CDRH2 comprises the amino acid sequence of SEQ ID NO: 92 or a variant thereof having one, two, or three deletions, additions, substitutions or the combinations thereof, the CDRH3 comprises the amino acid sequence of SEQ ID NO: 93 or a variant thereof having one, two, or three deletions, additions, substitutions or the combinations thereof, the CDRL1 comprises the amino acid sequence of SEQ ID NO: 94 or a variant thereof having one, two, or three deletions, additions, substitutions or the combinations thereof, the CDRL2 comprises the amino acid sequence of SEQ ID NO:

95 or a variant thereof having one, two, or three deletions, additions, substitutions or the combinations thereof, and the CDRL3 comprises the amino acid sequence of SEQ ID NO: 96 or a variant thereof having one, two, or three deletions, additions, substitutions or the combinations thereof.

In some embodiments, the heavy chain variable region comprises an amino acid sequence selected from the group consisting of SEQ ID NO:11 and 97-100, or a peptide having at least 90% sequence identity to an amino acid sequence selected from the group consisting of SEQ ID NO:11 and 97-100.

In some embodiments, the light chain variable region comprises an amino acid sequence selected from the group consisting of SEQ ID NO:12 and 101-102, or a peptide having at least 90% sequence identity to an amino acid sequence selected from the group consisting of SEQ ID NO: 12 and 101-102.

In one embodiment, the CDRs are those of 234B7D5, as exemplified in Tables 8B and 8D. In one embodiment, the CDRH1 comprises the amino acid sequence of SEQ ID NO: 103 or a variant thereof having one, two, or three deletions, additions, substitutions or the combinations thereof, the CDRH2 comprises the amino acid sequence of SEQ ID NO: 104 or a variant thereof having one, two, or three deletions, additions, substitutions or the combinations thereof, the CDRH3 comprises the amino acid sequence of SEQ ID NO: 105 or a variant thereof having one, two, or three deletions, additions, substitutions or the combinations thereof, the CDRL1 comprises the amino acid sequence of SEQ ID NO: 106 or a variant thereof having one, two, or three deletions, additions, substitutions or the combinations thereof, the CDRL2 comprises the amino acid sequence of SEQ ID NO: 107 or a variant thereof having one, two, or three deletions, additions, substitutions or the combinations thereof, and the CDRL3 comprises the amino acid sequence of SEQ ID NO: 108 or a variant thereof having one, two, or three deletions, additions, substitutions or the combinations thereof.

In some embodiments, the heavy chain variable region comprises an amino acid sequence selected from the group consisting of SEQ ID NO:13 and 109-112, or a peptide having at least 90% sequence identity to an amino acid sequence selected from the group consisting of SEQ ID NO:13 and 109-112.

In some embodiments, the light chain variable region comprises an amino acid sequence selected from the group consisting of SEQ ID NO:14 and 113-118, or a peptide having at least 90% sequence identity to an amino acid sequence selected from the group consisting of SEQ ID NO: 14 and 113-118.

The antibodies that contained these CDR regions, whether mouse, humanized or chimeric, had potent SIRPα binding and inhibitory activities. As shown in Example 5, certain residues within the CDR can be modified to retain or improve the property or reduce their potential to have post-translational modifications (PTMs). Such modified CDR can be referred to as affinity matured or de-risked CDRs.

Non-limiting examples of de-risked CDRs are provided in Tables 2B, 3B and 4B. Modified CDRs can include those having one, two or three amino acid addition, deletion and/or substitutions. In some embodiments, the substitutions can be conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE A

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| | | | | | | | | Amino Acid Similarity Matrix | | | | | | | | | | | | |
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 1 | 1 | 1 | | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

TABLE B

Conservative Amino Acid Substitutions

| For Amino Acid | Substitution With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-He, Met, D-Met |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemi-luminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as [152]Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Bi-Functional Molecules and Combination Therapies

An important component of the innate immune system is macrophages. Macrophages inhibit tumor growth through phagocytosis of tumor cells. Tumor cells can evade surveillance by macrophages by upregulating a "don't eat me" signal, CD47, on their cell surface. CD47 is ubiquitously expressed but is upregulated in various tumor types. By interacting with various ligands, CD47 has roles in the regulation of cell motility, adhesion, migration, and platelet activation. SIRPα is another member of the immunoglobulin superfamily and is primarily expressed on the surface of neurons and myeloid cells, including macrophages, granulocytes, monocytes, and dendritic cells. The CD47/SIRPα axis is a known major pathway for immune evasion by tumor cells.

Agents that target CD47 may initiate antibody opsonization, and activate antibody-dependent cellular cytotoxicity (ADCC) or antibody-dependent cellular phagocytosis (ADCP) which aids tumor cell destruction. However, due to the ubiquitous expression of CD47 may lead to RBC toxicity and other hematological adverse effects due to the presence of the antigen on the blood cells. Molecules targeting either SIRPα or bispecific agents that target both SIRPα and CD47 can be designed to elicit the ADCC and ADCP effect by possessing functional Fc domains.

Since SIRPα is more restricted in its expression compared to CD47, these molecules should not have as many hematological events as those targeting only CD47. Therefore, anti-SIRPα antibodies can be safer than anti-CD47 antibodies. Another option is the development of bispecific agents that target both the CD47/SIRPα axis and another tumor antigen. These agents can either be bispecific antibodies, fusion proteins and combination therapies.

Examples of tumor antigens, in particular those that can trigger tumor opsonizing, include CD19, CD20, EGFR, HER2, CD3, CD16, PD1, PD-L1, LAG3, TIM3, CTLA4, VISTA, CSFR1, A2AR, CD73, CD39, CD40, CEA, HER2, VEGFR, TIGIT, claudin18.2, CD24, GPC3, Il13RA2, 4-1BB, CCR8, and CMET, without limitation.

Different format of bispecific antibodies are also provided. In some embodiments, each of the anti-SIRPα fragment and the second fragment each is independently selected from a Fab fragment, a single-chain variable fragment (scFv), or a single-domain antibody. In some embodiments, the bispecific antibody further includes a Fc fragment.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The antibodies of the disclosure can also be used to treat or inhibit cancer. As provided above, SIRPα can be over-expressed in tumor cells, in particular gastric, pancreatic, esophageal, ovarian, and lung tumors. Inhibition of SIRPα has been shown to be useful for treating the tumors.

Accordingly, in some embodiments, provided are methods for treating a cancer in a patient in need thereof. The method, in one embodiment, entails administering to the patient an effective amount of an antibody of the present disclosure. In some embodiments, at least one of the cancer cells (e.g., stromal cells) in the patient over-express SIRPα.

Cellular therapies, such as chimeric antigen receptor (CAR) T-cell therapies, are also provided in the present disclosure. A suitable cell can be used, that is put in contact with an anti-SIRPα antibody of the present disclosure (or alternatively engineered to express an anti-SIRPα antibody of the present disclosure). Upon such contact or engineering, the cell can then be introduced to a cancer patient in need of a treatment. The cancer patient may have a cancer of any of the types as disclosed herein. The cell (e.g., T cell) can be, for instance, a tumor-infiltrating T lymphocyte, a CD4+ T cell, a CD8+ T cell, or the combination thereof, without limitation.

In some embodiments, the cell was isolated from the cancer patient him- or her-self. In some embodiments, the cell was provided by a donor or from a cell bank. When the cell is isolated from the cancer patient, undesired immune reactions can be minimized.

Non-limiting examples of cancers include bladder cancer, breast cancer, colorectal cancer, endometrial cancer, esophageal cancer, head and neck cancer, kidney cancer, leukemia, liver cancer, lung cancer, lymphoma, melanoma, pancreatic cancer, prostate cancer, and thyroid cancer. In some embodiments, the cancer is one or more of gastric, pancreatic, esophageal, ovarian, and lung cancers.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

The amount of the antibodies of the disclosure which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

As a general proposition, the dosage administered to a patient of the antigen-binding polypeptides of the present disclosure is typically 0.1 mg/kg to 100 mg/kg of the patient's body weight, between 0.1 mg/kg and 20 mg/kg of the patient's body weight, or 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the disclosure may be reduced by enhancing uptake and tissue penetration (e.g., into the brain) of the antibodies by modifications such as, for example, lipidation.

In an additional embodiment, the compositions of the disclosure are administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

In additional embodiments, the compositions of the disclosure are administered in combination with other therapeutic or prophylactic regimens, such as, for example, radiation therapy.

Diagnostic Methods

Over-expression of SIRPα is observed in certain tumor samples, and patients having SIRPα-over-expressing cells are likely responsive to treatments with the anti-SIRPα antibodies of the present disclosure. Accordingly, the antibodies of the present disclosure can also be used for diagnostic and prognostic purposes.

A sample that preferably includes a cell can be obtained from a patient, which can be a cancer patient or a patient desiring diagnosis. The cell be a cell of a tumor tissue or a tumor block, a blood sample, a urine sample or any sample from the patient. Upon optional pre-treatment of the sample, the sample can be incubated with an antibody of the present disclosure under conditions allowing the antibody to interact with a SIRPα protein potentially present in the sample. Methods such as ELISA can be used, taking advantage of the anti-SIRPα antibody, to detect the presence of the SIRPα protein in the sample.

Presence of the SIRPα protein in the sample (optionally with the amount or concentration) can be used for diagnosis of cancer, as an indication that the patient is suitable for a treatment with the antibody, or as an indication that the patient has (or has not) responded to a cancer treatment. For a prognostic method, the detection can be done at once, twice or more, at certain stages, upon initiation of a cancer treatment to indicate the progress of the treatment.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1: Generation of Murine Monoclonal Antibodies Against Human SIRPα

The human SIRPa protein was used to immunize different strains of mice and hybridomas were generated accordingly. Eight fusions were made to generate sufficient number of hybridoma clones. SIRPa v1/v2 positive binders were selected and subcloned. Subsequently, in vitro binding and functional screening were carried out with about 30 purified antibodies and lead antibodies with highest binding affinity and strongest functional potency were identified. The lead antibodies were humanized.

The VH/VL sequences of the lead murine antibodies are provided in the table below.

TABLE 1

| VH/VL sequence of the lead murine antibodies | | |
|---|---|---|
| Name | Sequence (CDRs are underlined) | SEQ ID NO: |
| 248G3F6 VH | EVQLQQSGAELVKPGASVKLSCTASGFNFEDTYMHWVKQRPDQGLEWIGR IDPADGDTKYNPKFQDKATITVDTSSNTAYLQLSSLTSEDTAVYYCVRGN YVNWGQGTTLTVSS | 1 |
| 248G3F6 VL | QIVLIQSPAIMSASPGERVTLTCRASSSVSSSYLYWYQQKPGSSPKLWIY STSNLASGVPARFSGSGSGTSYSLTISSMEAEDAASYFCHQWYSYPRTFG GGTKLEIK | 2 |
| 300A6A6 VH | QVQLQQSGTELVKPGSSVKISCKASGYTFTSNYIHWIRQQPGNGLEWIGW IYPGDGDTNYNQKFNGKATLTADKSSSTAYMQLSSLTSEDYAVYFCAINY GGIWFAYWGQGTLVTVSS | 3 |
| 300A6A6 VL | DIQMTQSPSSMSASLGDRVTITCQASQDIGNKLIWFQQKPGKSPRLMIHY VTNLPGGVPLRFSGSRSGSDYSLTISSLESEDMADYYCLQYKQNPLTFGS GTKLEIK | 4 |
| 102A10F2 VH | QVTLKESGPGILQPSQTLSLTCSFSGFSLNTYDIGMGWIRQPSGKGLEWL AHIWWNDREYYNSALQSRVTISKDTSNTQVFLKIASVDTADTATYYCVRI DYFGSGQAWFTYWGQGTLVTVSA | 5 |
| 102A10F2 VL | EIVLTQSPPTMAASPGEKITITCSSSSTISSTYLHWYQQKPGFSPKLLIS GTSNLASGVPPRFSGSGSGTSYSLTIGTLEAEDVATYYCQQGSRIPFTFG SGTKLEIK | 6 |
| 62D2H6 VH | EVQLQQSGAELVKPGASVKLSCTASGFNIKDYYMHWVKQRTEQGLEWIGR IDPEDGETKYAPKFQGKATITADTSSNTAYLQLSSLTSEDTAVYYCSRSW AYWGQGTTLTVSS | 7 |
| 62D2H6 VL | QIVLTQSPAIMSASPGEKVTLTCSASSSVSSSYLYWYQQKPGSSPKLWIY STSNLASGVPARFSGSGSGTSYSLTISSMEAEDAASYFCHQWSSYPRTFG GGTKLEIK | 8 |
| 211F8E11 VH | EVQLQQSGAELVKPGASVKLSCTASGFNIKDTYMHWVKQRPEQGLEWVGR IDPANVNTIYDPKFQGKATITADTSSNTAYLQLSSLTSEDTAVYYCARVG AYDGYDFDYWGQGTTLTVSS | 9 |

TABLE 1-continued

VH/VL sequence of the lead murine antibodies

| Name | Sequence (CDRs are underlined) | SEQ ID NO: |
|------|--------------------------------|------------|
| 211F8E11 VL | DIVLTQSPASLAVSLGQRATISCRASESVDNYGNSFMHWYQQKPGQPPKL LIYRASNLESGIPARFSGSGSRTDFTLTINPVEADDVATYYCQQNNEDPL TFGAGTKLELK | 10 |
| 217D11E5 VH | EVQLQQSGPELVKPGASVKMSCKASGYTFTSYVMHWVKQKPGQGLEWIGY INPYNDGTKYNEKFKGKATLTSDKSSSTAYMELSSLTSEDSAVYYCARSY YDYDGSFDYWGQGTTLTVSS | 11 |
| 217D11E5 VL | DIVMTQSHKFMSTSVGDRVSITCKASQDVTTAVAWYQQKSGQSPKLLIYS ASYRYTGDPDRFTGSGSGTDFTFTISSVQAEDLAVYYCQQHYSTPWTFGG GTKLEIK | 12 |
| 234B7D5 VH | EVQLQQSGAELVKPGASVKLSCTASGFNFEDTYIHWVKQRPDQGLEWIGR IDPADGDTKHNPKFHDKATVTVDTSSNTAYLELSSLTSEDTAVYYCVRGN YVNWGQGTTLTVSS | 13 |
| 234B7D5 VL | QIVLIQSPAIMSASPGERVTLTCRASSSVTSSYLYWYQQKPGSSPKLWIY SASNLASGVPARFSGSGSGTSYSLTISSVEAEDAASYFCHQWYSYPRTFG GGTKLEIK | 14 |

Example 2. Cross-binding of SIRPa v1 and v2

This example measured the dose response of ELISA binding of mouse anti-SIRPα mAb to recombinant human SIRPα variant 1 and variant 2 protein (0.5 µg/ml@100 µl). Recombinant human SIRPα v1 or v2 protein (Biointron) was coated at 0.5 µg/ml in PBS onto microtiter plates for 2 h at RT. After coating of the antigen, the wells were blocked with PBS/0.05% Tween (PBST) with 1% BSA for 1 h at RT.

After washing of the wells with PBST, different concentrations of anti-SIRPα antibodies were added to the well and incubated for 1 at RT. For detection of the binding antibodies, the HRP conjugated secondary antibodies against mouse Fc (Jackson Immuno Research) were added followed by the addition of fluorogenic substrates (Roche). Between all incubation steps, the wells of the plate were washed with PBST three times. Fluorescence was measured in a TECAN Spectrafluor plate reader.

The results are shown in FIG. 1. Both tested antibodies, 248G3F6 and 300A6A6, exhibited nanogram level affinity to both variants 1 and 2.

The binding kinetics assay of antibody to variant 1 was performed using Biacore 8K system through human antibody capture approach. The anti-mouse Fc IgG were immobilized on CM5 sensor chip according to the manufactory's instruction. The test antibody was injected and captured by the immobilized anti-human Fc IgG. Serial concentrations of antigen was individually injected, and the binding profile was recorded for each concentration antigen analyte, respectively.

The assay system was regenerated by injection of 10 mM Glycine-HCl pH 1.5 for 30 seconds. The running buffer was HBS-EP+ (10 mM HEPES, pH 7.4, 150 mM NaCl, 3 mM EDTA and 0.05% P20). The assay temperature was 25° C., and the association and dissociation time were 180 and 600 seconds, respectively. The Biacore data were fitted using Biacore K8 evaluation software 1.0 according to 1:1 binding model to calculate the association (ka) and dissociation (kd) rate constants as well as the equilibrium constant (KD).

Figure 2:
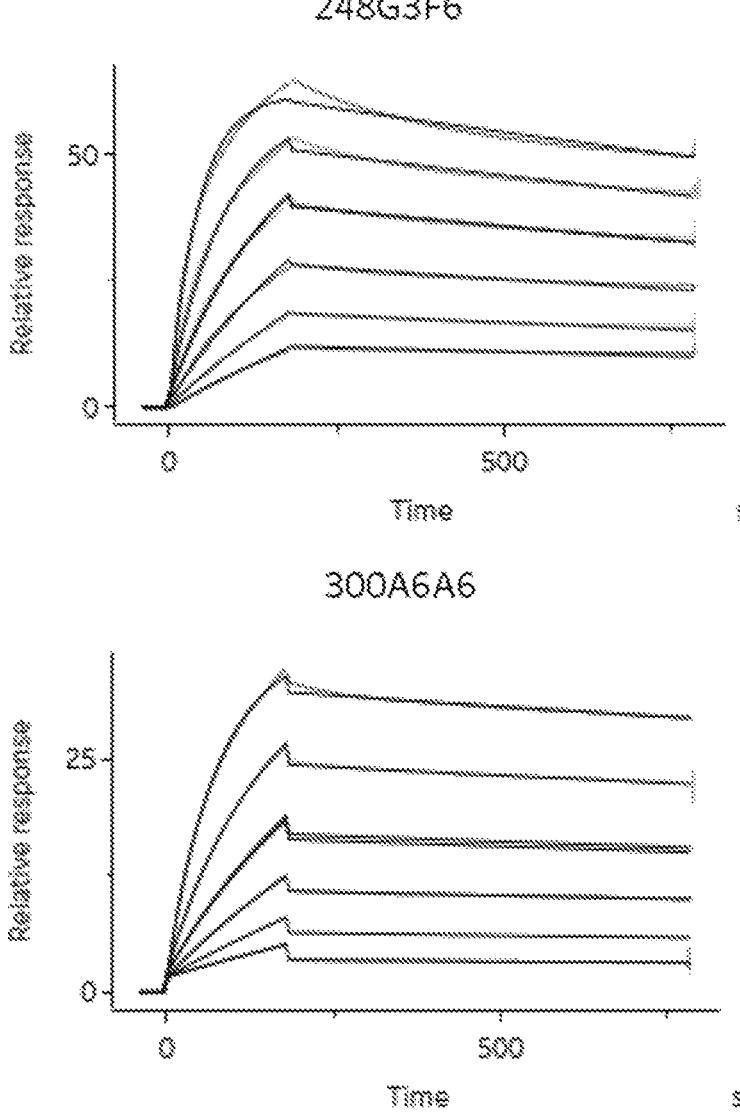
FIG. 2 shows binding affinity of the antibody against SIRPa v1.

The results are shown in FIG. 2, and summarized in the table below. Both tested antibodies exhibited excellent binding affinity.

| Sample | ka (1/Ms) | kd (1/s) | KD (M) |
|--------|-----------|----------|--------|
| 248G3F6 | 1.87E+05 | 3.74E−04 | 2.00E−09 |
| 300A6A6 | 1.31E+05 | 1.48E−04 | 1.13E−09 |

Example 3. Competition with CD47

This example tested the ability of the anti-SIRPα antibodies to compete with CD47 in binding to SIRPα.

Recombinant CD47-Fc fusion protein (Acrobiosystems) was coated at 1 µg/ml in PBS onto microtiter plates for 16 hours at 4° C. After blocking for 1 h with 1% BSA in PBST at RT, 1 µg/mL of SIRPα-His protein was added either in the absence or presence of different concentrations of anti-SIRPα antibodies at RT for 1 h. Plates were subsequently washed three times and incubated with an HRP-conjugated anti-His secondary antibody for 1 h at RT. After washing, the TMB solution was added to each well for 30 min and the reaction was stopped with 2M H2504, and OD was measured at 490 nm.

Figure 3:
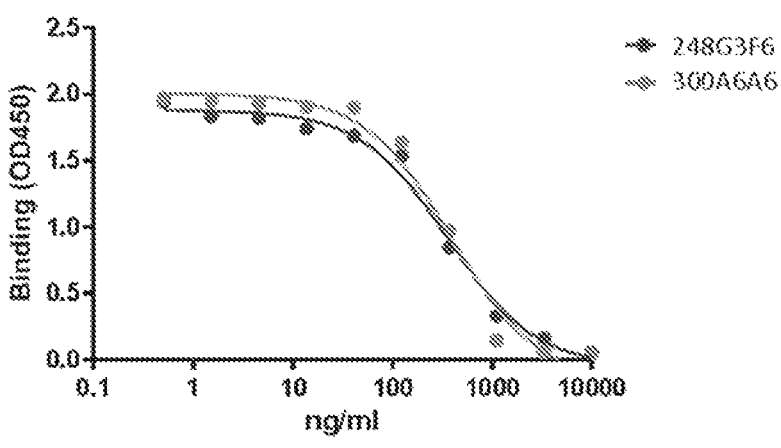
FIG. 3 shows competition of SIRPα interaction with CD47 by the antibodies.

As shown in FIG. 3, both 248G3F6 and 300A6A6 potently and dose-dependently inhibited the binding of CD47 to SIRPα.

Example 4. Induction of Macrophage Mediated Phagocytosis

This example tested the ability of the anti-SIRPα antibodies to induce macrophage mediated phagocytosis.

PBMCs were isolated from human blood, and the monocytes were differentiated into macrophages for 6 days. The monocyte derived macrophages (MDMs) were scraped and re-plated in 24-well dishes and allowed to adhere for 24 hours. The human tumor cell line Raji which endogenously expressed CD47 were transfected with human PD-L1 to overexpress human PD-L1 on the surface. This PD-L1 overexpressed Raji cells were chosen as target cells and labeled with 1 µM CFSE for 10 minutes, then added to MDMs at a ratio of 5:1 tumor cells per phagocyte.

Anti-SIRPalpha antibodies and anti-PD-L1 antibody were added in the culture system. After incubation for 3 hours, non-phagocytosed target cells were washed away with PBS and the remaining phagocytes were scraped off, stained with macrophage marker C76 antibody, and analyzed by flow cytometry. Phagocytosis was measured by gating on C76⁺ cells and then assessing the percent of CFSE⁺ cells.

Figure 4:
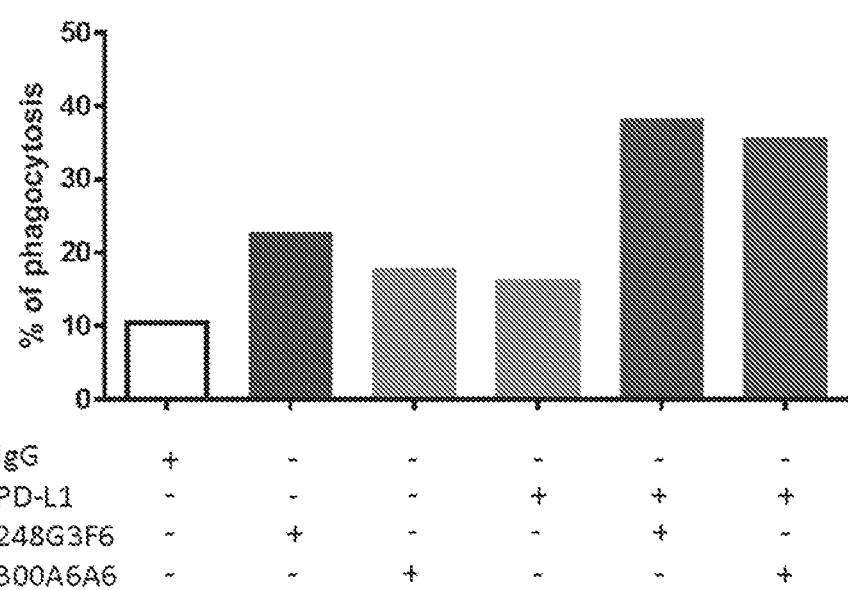
FIG. 4 shows induction of macrophage mediated phagocytosis by the antibodies.

The results of phagocytosis of PD-L1 expressing tumor cells by combo-treatment of anti-SIRPα antibody with anti-PD-L1 antibody are shown in FIG. 4. The combination of anti-PD-L1 antibody with either of the anti-SIRPα antibodies exhibited the highest phagocytosis (the two columns on the right).

Example 5. Humanization of the Mouse mAbs

The murine antibody variable region genes were employed to create humanized mAbs. In the first step of this process, the amino acid sequences of the VH and VL of mAb were compared against the available database of human Ig gene sequences to find the overall best-matching human germline Ig gene sequences.

The amino acid sequences of the humanized antibody are provided below.
Humanized Sequences
A. 248G3F6

TABLE 2A

| | Humanization of 248G3F6-VH | |
|---|---|---|
| Name | Sequence | SEQ ID NO: |
| 248G3F6 VH | EVQLQQSGAELVKPGASVKLSCTASGFNFEDTYMHWVKQRPDQGLEWIGR IDPADGDTKYNPKFQDKATITVDTSSNTAYLQLSSLTSEDTAVYYCVRGN YVNWGQGTTLTVSS | 1 |
| V1 (CDR grafting) | QVQLVQSGAEVKKPGASVKVSCKASGFNFEDTYMHWVRQAPGQGLEWMGR IDPADGDTKYNPKFQDRVTMTRDTSTSTVYMELSSLRSEDTAVYYCARGN YVNWGQGTTVTVSS | 23 |
| V2 (with back mutations) | QVQLVQSGAEVKKPGASVKVSCKASGFNFEDTYMHWVRQAPGQGLEWMGR IDPADGDTKYNPKFQDRVTMTVDTSTNTAYMELSSLRSEDTAVYYCVRGN YVNWGQGTTVTVSS | 24 |
| V3 (with back mutations) | QVQLVQSGAEVKKPGASVKVSCKASGFNFEDTYMHWVRQAPGQGLEWMGR IDPADGDTKYNPKFQDRVTITVDTSTNTAYMELSSLRSEDTAVYYCVRGN YVNWGQGTTVTVSS | 25 |
| V4 (with back mutations) | QVQLVQSGAEVKKPGASVKVSCKASGFNFEDTYMHWVRQAPGQGLEWMGR IDPAEGDTKYNPKFQDRVTITVDTSTNTAYMELSSLRSEDTAVYYCVRGN YVNWGQGTTVTVSS | 26 |
| V5 (with back mutations) | QVQLVQSGAEVKKPGASVKVSCKASGFNFEDTYMHWVRQAPGQGLEWMGR IDPADADTKYNPKFQDRVTITVDTSTNTAYMELSSLRSEDTAVYYCVRGN YVNWGQGTTVTVSS | 27 |

TABLE 2B

| | CDR Sequences | | |
|---|---|---|---|
| | CDR | Sequence | SEQ ID NO: |
| | CDR-H1 | DTYMH | 15 |
| | CDR-H2 | RIDPADGDTKYNPKFQD | 16 |
| | CDR-H3 | GNYVN | 17 |
| | CDR-H2(v4) | RIDPAEGDTKYNPKFQD | 21 |
| | CDR-H2(v5) | RIDPADADTKYNPKFQD | 22 |

TABLE 2C

| | Humanization of 248G3F6-VL | |
|---|---|---|
| Name | Sequence | SEQ ID NO: |
| 248G3F6 VL | QIVLIQSPAIMSASPGERVTLTCRASSSVSSSYLYWYQQKPGSSPKLWIY STSNLASGVPARFSGSGSGTSYSLTISSMEAEDAASYFCHQWYSYPRTFG GGTKLEIK | 2 |
| V1 (CDR grafting) | EIVLTQSPGTLSLSPGERATLSCRASSSVSSSYLYWYQQKPGQAPRLLIY STSNLASGIPDRFSGSGSGTDFTLTISRLEPEDFAVYYCHQWYSYPRTFG GGTKVEIK | 28 |

TABLE 2C-continued

| Humanization of 248G3F6-VL | | |
|---|---|---|
| Name | Sequence | SEQ ID NO: |
| V2 (with back mutations) | EIVLTQSPGTLSLSPGERATLSCRASSSVSSSYLYWYQQKPGQAPRLLIY STSNLASGIPDRFSGSGSGTDYTLTISRLEPEDAAVYFCHQWYSYPRTFG GGTKVEIK | 29 |

TABLE 2D

| CDR Sequences | | |
|---|---|---|
| CDR | Sequence | SEQ ID NO: |
| CDR-L1 | RASSSVSSSYLY | 18 |
| CDR-L2 | STSNLAS | 19 |
| CDR-L3 | HQWYSYPRT | 20 |

TABLE 2E

| Humanized antibodies | | | |
|---|---|---|---|
| | VL | VL v1 | VL v2 |
| VH | HSP210-02-Chi | | |
| VH v1 | | HSP210-02-hz11 | HSP210-02-hz12 |
| VH v2 | | HSP210-02-hz21 | HSP210-02-hz22 |
| VH v3 | | HSP210-02-hz31 | HSP210-02-hz32 |
| VH v4 | | HSP210-02-hz41 | HSP210-02-hz42 |
| VH v5 | | HSP210-02-hz51 | HSP210-02-hz52 |

B. 300A6A6

TABLE 3A

| Humanization of 300A6A6-VH | | |
|---|---|---|
| Name | Sequence | SEQ ID NO: |
| 300A6A6 VH | QVQLQQSGTELVKDGSSVKISCKASGYTFTSNYIHWIRQQDGNGLEWIGW IYPGDGDTNYNQKFNGKATLTADKSSSTAYMQLSSLTSEDYAVYFCAINY GGIWFAYWGQGTLVTVSS | 3 |
| V1 (CDR grafting) | QVQLVQSGAEVKKDGSSVKVSCKASGYTFTSNYIHWVRQADGQGLEWMGW IYPGDGDTNYNQKENGRVTITADKSTSTAYMELSSLRSEDTAVYYCARNY GGIWFAYWGQGTLVTVSS | 39 |
| V2 (with back mutations) | QVQLVQSGAEVKKDGSSVKVSCKASGYTFTSNYIHWVRQADGQGLEWMGW IYDGDGDTNYNQKFNGRVTITADKSTSTAYMELSSLRSEDTAVYYCAINY GGIWFAYWGQGTLVTVSS | 40 |
| V3 (with back mutations) | QVQLVQSGAEVKKDGSSVKVSCKASGYTFTSNYIHWVRQADGQGLEWMGW IYDGDGDTNYNQKFNGRVTLTADKSTSTAYMELSSLRSEDTAVYYCAINY GGIWFAYWGQGTLVTVSS | 41 |
| V4 (with back mutations) | QVQLVQSGAEVKKDGSSVKVSCKASGYTFTSNYIHWVRQADGQGLEWMGW IYDGEGDTNYNQKFNGRVTLTADKSTSTAYMELSSLRSEDTAVYYCAINY GGIWFAYWGQGTLVTVSS | 42 |
| V5 (with back mutations) | QVQLVQSGAEVKKDGSSVKVSCKASGYTFTSNYIHWVRQADGQGLEWMGW IYDGDADTNYNQKFNGRVTLTADKSTSTAYMELSSLRSEDTAVYYCAINY GGIWFAYWGQGTLVTVSS | 43 |
| V6 (with back mutations) | QVQLVQSGAEVKKDGSSVKVSCKASGYTFTSNYIHWVRQADGQGLEWMGW IYDGDGDTNYNQKFQGRVTLTADKSTSTAYMELSSLRSEDTAVYYCAINY GGIWFAYWGQGTLVTVSS | 44 |

TABLE 3B

| | CDR Sequences | |
|---|---|---|
| CDR | Sequence | SEQ ID NO: |
| CDR-H1 | SNYIH | 30 |
| CDR-H2 | WIYPGDGDTNYNQKFNG | 31 |
| CDR-H3 | NYGGIWFAY | 32 |
| CDR-H2(v4) | WIYPGEGDTNYNQKFNG | 36 |
| CDR-H2(v5) | WIYPGDADTNYNQKFNG | 37 |
| CDR-H2(v6) | WIYPGDGDTNYNQKFQG | 38 |

TABLE 3C

| | Humanization of 300A6A6-VL | |
|---|---|---|
| Name | Sequence | SEQ ID NO: |
| 300A6A6 VL | DIQMTQSPSSMSASLGDRVTITCQASQDTGNKLIWFQQKPGKSPRLMIHY VTNLPGGVPLRFSGSRSGSDYSLTISSLESEDMADYYCLQYKQNPLTFGS GTKLEIK | 4 |
| V1 (CDR grafting) | DIQMTQSPSSLSASVGDRVTITCQASQDIGNKLIWYQQKPGKAPKLLIYY VTNLPGGVPSRFSGSGSGTDFTLTISSLQPEDFATYYCLQYKQNPLTFGQ GTKLEIK | 45 |
| V2 (with back mutations) | DIQMTQSPSSLSASVGDRVTITCQASQDIGNKLIWFQQKPGKAPKLLIHY VTNLPGGVPSRFSGSRSGSDYTLTISSLQPEDFATYYCLQYKQNPLTFGQ GTKLEIK | 46 |

TABLE 3D

| | CDR Sequences | |
|---|---|---|
| CDR | Sequence | SEQ ID NO: |
| CDR-L1 | QASQDIGNKLI | 33 |
| CDR-L2 | YVTNLPG | 34 |
| CDR-L3 | LQYKQNPLT | 35 |

TABLE 3E

| | Humanized antibodies | | |
|---|---|---|---|
| | VL | VL v1 | VL v2 |
| VH | HSP210-03-Chi | | |
| VH v1 | | HSP210-03-hz11 | HSP210-03-hz12 |
| VH v2 | | HSP210-03-hz21 | HSP210-03-hz22 |
| VH v3 | | HSP210-03-hz31 | HSP210-03-hz32 |
| VH v4 | | HSP210-03-hz41 | HSP210-03-hz42 |
| VH v5 | | HSP210-03-hz51 | HSP210-03-hz52 |
| VH v6 | | HSP210-03-hz61 | HSP210-03-hz62 |

C. 102A10F2

TABLE 4A

| | Humanization of 102A10F2-VH | |
|---|---|---|
| Name | Sequence | SEQ ID NO: |
| 102A10F2 VH | QVTLKESGPGILQPSQTLSLTCSFSGFSLNTYDIGMGWIRQPSGKGLEWLAH IWWNDREYYNSALQSRVTISKDTSNTQVFLKIASVDTADTATYYCVRIDYFG SGQAWFTYWGQGTLVTVSA | 5 |
| V1 (CDR grafting) | QLQLQESGPGLVKPSETLSLTCTVSGFSLNTYDIGMGWIRQPPGKGLEWIGH IWWNDREYYNSALQSRVTISVDTSKNQFSLKLSSVTAADTAVYYCARIDYFG SGQAWFTYWGQGTLVTVSS | 55 |
| V2 (with back mutations) | QVQLQESGPGLVKPSETLSLTCTFSGFSLNTYDIGMGWIRQPPGKGLEWIGH IWWNDREYYNSALQSRVTISKDTSKTQVSLKLSSVTAADTAVYYCVRIDYFG SGQAWFTYWGQGTLVTVSS | 56 |
| V3 (with back mutations) | QVQLQESGPGLVKPSETLSLTCTFSGFSLNTYDIGMGWIRQPPGKGLEWIAH IWWNDREYYNSALQSRVTISKDTSKTQVSLKLSSVTAADTAVYYCVRIDYFG SGQAWFTYWGQGTLVTVSS | 57 |

TABLE 4A-continued

Humanization of 102A10F2-VH

| Name | Sequence | SEQ ID NO: |
|---|---|---|
| V4 (with back mutations) | QVQLQESGPGLVKPSETLSLTCTFSGFSLSTYDIGMGWIRQPPGKGLEWIAH IWWNDREYYNSALQSRVTISKDTSKTQVSLKLSSVTAADTAVYYCVRIDYFG SGQAWFTYWGQGTLVTVSS | 58 |
| V5 (with back mutations) | QVQLQESGPGLVKPSETLSLTCTFSGFSLNTYDIGMGWIRQPPGKGLEWIAH IWWNDREYYSSALQSRVTISKDTSKTQVSLKLSSVTAADTAVYYCVRIDYFG SGQAWFTYWGQGTLVTVSS | 59 |
| V6 (with back mutations) | QVQLQESGPGLVKPSETLSLTCTFSGFSLNTYDIGMGWIRQPPGKGLEWIAH IWWNDREYYNPALQSRVTISKDTSKTQVSLKLSSVTAADTAVYYCVRIDYFG SGQAWFTYWGQGTLVTVSS | 60 |

TABLE 4B

CDR Sequences

| CDR | Sequence | SEQ ID NO: |
|---|---|---|
| CDR-H1 | TYDIGMG | 47 |
| CDR-H2 | HIWWNDREYYNSALQS | 48 |
| CDR-H3 | IDYFGSGQAWFTY | 49 |
| CDR-H2 (v5) | HIWWNDREYYSSALQS | 53 |
| CDR-H2 (v6) | HIWWNDREYYNPALQS | 54 |

TABLE 4C

Humanization of 102A10F2-VL

| Name | Sequence | SEQ ID NO: |
|---|---|---|
| 102A10F2 VL | EIVLTQSPPTMAASPGEKITITCSSSSTISSTYLHWYQQKPGFSPKLLIS GTSNLASGVPPRFSGSGSGTSYSLTIGTLEAEDVATYYCQQGSRIPFTFG SGTKLEIK | 6 |
| V1 (CDR grafting) | EIVLTQSPGTLSLSPGERATLSCSSSSTISSTYLHWYQQKPGQAPRLLIY GTSNLASGIPDRFSGSGSGTDFTLTISRLEPEDFAVYYCQQGSRIPFTFG QGTKLEIK | 61 |
| V2 (withback mutations) | EIVLTQSPGTLSLSPGERATLSCSSSSTISSTYLHWYQQKPGQAPRLLIS GTSNLASGIPDRFSGSGSGTDYTLTISRLEPEDVAVYYCQQGSRIPFTFG QGTKLEIK | 62 |

TABLE 4D

CDR Sequences

| CDR | Sequence | SEQ ID NO: |
|---|---|---|
| CDR-L1 | SSSSTISSTYLH | 50 |
| CDR-L2 | GTSNLAS | 51 |
| CDR-L3 | QQGSRIPFT | 52 |

TABLE 3E

Humanized antibodies

| | VL | VL v1 | VL v2 |
|---|---|---|---|
| VH | HSP210-01-Chi | | |
| VH v1 | | HSP210-01-hz11 | HSP210-01-hz12 |
| VH v2 | | HSP210-01-hz21 | HSP210-01-hz22 |
| VH v3 | | HSP210-01-hz31 | HSP210-01-hz32 |
| VH v4 | | HSP210-01-hz41 | HSP210-01-hz42 |
| VH v5 | | HSP210-01-hz51 | HSP210-01-hz52 |
| VH v6 | | HSP210-01-hz61 | HSP210-01-hz62 |

D. 62D2116

TABLE 5A

| | Humanization of 62D2H6-VH | |
| --- | --- | --- |
| Name | Sequence | SEQ ID NO: |
| 62D2H6 VH | EVQLQQSGAELVKPGASVKLSCTASGFNIKDYYMHWVKQRTEQGLEWIGR IDPEDGETKYAPKFQGKATITADTSSNTAYLQLSSLTSEDTAVYYCSRSW AYWGQGTTLTVSS | 7 |
| V1 (CDR grafting) | EVQLVQSGAEVKKPGATVKISCKVSGFNIKDYYMHWVQQAPGKGLEWMGR IDPEDGETKYAPKFQGRVTITADTSTDTAYMELSSLRSEDTAVYYCATSW AYWGQGTTVTVSS | 69 |
| V2 (with back mutations) | EVQLVQSGAEVKKPGATVKISCKASGFNTKDYYMHWVQQAPGKGLEWMGR IDPEDGETKYAPKFQGRVTITAD̲TS̲TNTAYMELSSLRSEDTAVYYCSRSW AYWGQGTTVTVSS | 70 |
| V3 (chimeric 2) | QVQLVQSGAEVKKPGASVKVSCKASGFNIKDYYMHWVRQAPGQGLEWMGR I̲DPEDGETKYAPKFQGR̲VTMTRDT̲STSTVYMELSSLRS̲EDTAVYYCAR̲SW AYWGQGTTVTVSS | 71 |
| V4 (with back mutations) | QVQLVQSGAEVKKPGASVKVSCKASGFNIKDYYMHWVRQAPGQGLEWMGR IDPEDGETKYAPKFQGR̲VTMTAD̲TS̲TNTAYMELSSLRS̲EDTAVYYCSRSW AYWGQGTTVTVSS | 72 |

TABLE 5B

| | CDR Sequences | |
| --- | --- | --- |
| CDR | Sequence | SEQ ID NO: |
| CDR-H1 | DYYMH | 63 |
| CDR-H2 | RIDPEDGETKYAPKFQG | 64 |
| CDR-H3 | SWAY | 65 |

TABLE 5C

| | Humanization of 62D2H6-VL | |
| --- | --- | --- |
| Name | Sequence | SEQ ID NO: |
| 62D2H6 VL | QIVLTQSPAIMSASPGEKVTLTCSASSSVSSSYLYWYQQKPGSSPKLWIYST SNLASGVPARFSGSGSGTSYSLTISSMEAEDAASYFCHQWSSYPRTFGGGTK LEIK | 8 |
| V1 (CDR grafting) | EIVLTQSPATLSLSPGERATLSCSASSSVSSSYLYWYQQKPGQAPRLLIYST SNLASGIPARFSGSGSGTDFTLTISSLEPEDFAVYYCHQWSSYPRTFGGGTK VEIK | 73 |
| V2 (with back mutations) | EIVLTQSPATLSLSPGERATLSCSASSSVSSSYLYWYQQKPGQAPRLLIYST SNLASGIPARFSGSGSGTDYTLTISSLEPEDAAVYFCHQWSSYPRTFGGGTK VEIK | 74 |
| V3 (chimeric 2) | EIVMTQSPPTLSLSPGERVTLSCSASSSVSSSYLYWYQQKPGQAPRLLIYST SNLASGIPARFSGSGSGTDFTLTISSLQPEDFAVYYCHQWSSYPRTFGGGTK VEIK | 75 |
| V4 (with back mutations) | EIVMTQSPPTLSLSPGERVTLSCSASSSVSSSYLYWYQQKPGQAPRLLIYST SNLASGIPARFSGSGSGTDYTLTISSLQPEDAAVYFCHQWSSYPRTFGGGTK VEIK | 76 |

TABLE 5D

| CDR Sequences | | |
|---|---|---|
| CDR | Sequence | SEQ ID NO: |
| CDR-L1 | SASSSVSSSYLY | 66 |
| CDR-L2 | STSNLAS | 67 |
| CDR-L3 | HQWSSYPRT | 68 |

TABLE 5E

| Humanized antibodies | | | | | |
|---|---|---|---|---|---|
| | VL | VL v1 | VL v2 | VL v3 | VL v4 |
| VH | Chimeric | | | | |
| VH v1 | | hz11 | | | |
| VH v2 | | | hz22 | | hz24 |
| VH v3 | | | | hz33 | |
| VH v4 | | | hz42 | | hz44 |

E. 211F8E11

TABLE 6A

| Humanization of 211F8E11-VH | | |
|---|---|---|
| Name | Sequence | SEQ ID NO: |
| 211F8E11 VH | EVQLQQSGAELVKPGASVKLSCTASGFNIKDTYMHWVKQRPEQGLEWVGR IDPANVNTIYDPKFQGKATITADTSSNTAYLQLSSLTSEDTAVYYCARVG AYDGYDFDYWGQGTTLTVSS | 9 |
| V1 (CDR grafting) | EVQLVQSGAEVKKPGATVKISCKVSGFNIKDTYMHWVQQAPGKGLEWMGR IDPANVNTIYDPKFQGRVTITADTSTDTAYMELSSLRSEDTAVYYCATVG AYDGYDFDYWGQGTTVTVSS | 83 |
| V2 (with back mutations) | EVQLVQSGAEVKKPGATVKISCKASGFNIKDTYMNWVQQAPGKGLEWMGR IDPANVNTIYDPKFQGRVTITADTSTNTAYMELSSLRSEDTAVYYCARVG AYDGYDFDYWGQGTTVTVSS | 84 |
| V3 (chimeric 2) | QVQLVQSGAEVKKPGASVKVSCKASGFNIKDTYMNWVRQAPGQGLEWMGR IDPANVNTIYDPKFQGRVTMTRDTSTSTVYMELSSLRSEDTAVYYCARVG AYDGYDFDYWGQGTTVTVSS | 85 |
| V4 (with back mutations) | QVQLVQSGAEVKKPGASVKVSCKASGFNIKDTYMNWVRQAPGQGLEWMGR IDPANVNTIYDPKFQGRVTMTADTSTNTAYMELSSLRSEDTAVYYCARVG AYDGYDFDYWGQGTTVTVSS | 86 |

TABLE 6B

| CDR Sequences | | |
|---|---|---|
| CDR | Sequence | SEQ ID NO: |
| CDR-H1 | DTYMH | 77 |
| CDR-H2 | RIDPANVNTIYDPKFQG | 78 |
| CDR-H3 | VGAYDGYDFDY | 79 |

TABLE 6C

| Humanization of 211F8E11-VL | | |
|---|---|---|
| Name | Sequence | SEQ ID NO: |
| 211F8E11 VL | DIVLTQSPASLAVSLGQRATISCRASESVDNYGNSFMHWYQQKPGQPPKLLI YRASNLESGIPARFSGSGSRTDFTLTINPVEADDVATYYCQQNNEDPLTFGA GTKLELK | 10 |
| V1 (CDR grafting) | DIVMTQSPDSLAVSLGERATINCRASESVDNYGNSFMHWYQQKPGQPPKLLI YRASNLESGVPDRFSGSGSGTDFTLTISSLQAEDVAVYYCQQNNEDPLTFGQ GTKLEIK | 87 |
| V2 (with back mutations) | DIVLTQSPDSLAVSLGERATINCRASESVDNYGNSFMHWYQQKPGQPPKLLI YRASNLESGVPDRFSGSGSRTDFTLTISSLQAEDVAVYYCQQNNEDPLTFGQ GTKLEIK | 88 |
| V3 (chimeric 2) | DIQMTQSPSSLSASVGDRVTITCRASESVDNYGNSFMHWYQQKPGKVPKLLI YRASNLESGVPSRFSGSGSGTDFTLTISSLQPEDVATYYCQQNNEDPLTFGQ GTKLEIK | 89 |

TABLE 6C-continued

Humanization of 211F8E11-VL

| Name | Sequence | SEQ ID NO: |
|---|---|---|
| V4 (with back mutations) | DIQLTQSPSSLSASVGDRVTITCRASESVDNYGNSFMHWYQQKPGKVPKLLI<br>YRASNLESGVPSRFSGSGSRTDFTLTISSLQPEDVATYYCQQNNEDPLTFGQ<br>GTKLEIK | 90 |

TABLE 6D

CDR Sequences

| CDR | Sequence | SEQ ID NO: |
|---|---|---|
| CDR-L1 | RASESVDNYGNSFMH | 80 |
| CDR-L2 | RASNLES | 81 |
| CDR-L3 | QQNNEDPLT | 82 |

TABLE 6E

Humanized antibodies

|  | VL | VL v1 | VL v2 | VL v3 | VL v4 |
|---|---|---|---|---|---|
| VH | Chimeric | | | | |
| VH v1 | | hz11 | | | |
| VH v2 | | | hz22 | | hz24 |
| VH v3 | | | | hz33 | |
| VH v4 | | | hz42 | | hz44 |

F. 217D11E5

TABLE 7A

Humanization of 217D11E5-VH

| Name | Sequence | SEQ ID NO: |
|---|---|---|
| 217D11E5 VH | EVQLQQSGPELVKPGASVKMSCKASGYTFTSYVMHWVKQKPGQGLEWIGY<br>INPYNDGTKYNEKFKGKATLTSDKSSSTAYMELSSLTSEDSAVYYCARSY<br>YDYDGSFDYWGQGTTLTVSS | 11 |
| V1 (CDR grafting) | QVQLVQSGAEVKKPGASVKVSCKASGYTFTSYVMHWVRQAPGQRLEWMGY<br>INPYNDGTKYNEKFKGRVTITRDTSASTAYMELSSLRSEDTAVYYCARSY<br>YDYDGSFDYWGQGTTVTVSS | 97 |
| V2 (with back mutations) | QVQLVQSGAEVKKPGASVKVSCKASGYTFTSYVMHWVRQAPGQRLEWMGY<br>INPYNDGTKYNEKFKGRVTITSDKSASTAYMELSSLRSEDTAVYYCARSY<br>YDYDGSFDYWGQGTTVTVSS | 98 |
| V3 (chimeric 2) | QVQLVQSGAEVKKPGASVKVSCKASGYTFTSYVMHWVRQAPGQGLEWMGY<br>INPYNDGTKYNEKFKGRVTMTRDTSTSTVYMELSSLRSEDTAVYYCARSY<br>YDYDGSFDYWGQGTTVTVSS | 99 |
| V4 (with back mutations) | QVQLVQSGAEVKKPGASVKVSCKASGYTFTSYVMHWVRQAPGQGLEWMGY<br>INPYNDGTKYNEKFKGRVTMTSDKSTSTAYMELSSLRSEDTAVYYCARSY<br>YDYDGSFDYWGQGTTVTVSS | 100 |

TABLE 7B

CDR Sequences

| CDR | Sequence | SEQ ID NO: |
|---|---|---|
| CDR-H1 | SYVMH | 91 |
| CDR-H2 | YINPYNDGTKYNEKFKG | 92 |
| CDR-H3 | SYYDYDGSFDY | 93 |

TABLE 7C

Humanization of 217D11E5-VL

| Name | Sequence | SEQ ID NO: |
|---|---|---|
| 217D11E5 VL | DIVMTQSHKFMSTSVGDRVSITCKASQDVTTAVAWYQQKSGQSPKLLIYSAS<br>YRYTGDPDRFTGSGSGTDFTFTISSVQAEDLAVYYCQQHYSTPWTFGGGTKL<br>EIK | 12 |

TABLE 7C-continued

| Humanization of 217D11E5-VL | | |
|---|---|---|
| Name | Sequence | SEQ ID NO: |
| V1 (CDR grafting) | DIQMTQSPSSLSASVGDRVTITCKASQDVTTAVAWYQQKPGKAPKLLIYSAS YRYTGVPSRFSGSGSGTDFTFTISSLQPEDIATYYCQQHYSTPWTFGGGTKV EIK | 101 |
| V2 (chimeric 2) | DIQMTQSPSSLSASVGDRVTITCKASQDVTTAVAWYQQKPGKVPKLLIYSAS YRYTGVPSRFSGSGSGTDFTLTISSLQPEDVATYYCQQHYSTPWTFGGGTKV EIK | 102 |

TABLE 7D

| CDR Sequences | | |
|---|---|---|
| CDR | Sequence | SEQ ID NO: |
| CDR-L1 | KASQDVTTAVA | 94 |
| CDR-L2 | SASYRYT | 95 |
| CDR-L3 | QQHYSTPWT | 96 |

TABLE 7E

| Humanized antibodies | | | |
|---|---|---|---|
| | VL | VL v1 | VL v2 |
| VH | Chimeric | | |
| VH v1 | | hz11 | |
| VH v2 | | hz21 | hz22 |
| VH v3 | | | |
| VH v4 | | hz41 | hz42 |

G. 234B7D5

TABLE 8A

| Humanization of 234B7D5-VH | | |
|---|---|---|
| Name | Sequence | SEQ ID NO: |
| 234B7D5 VH | EVQLQQSGAELVKPGASVKLSCTASGFNFEDTYIHWVKQRPDQGLEWIGRID PADGDTKHNPKFHDKATVTVDTSSNTAYLELSSLTSEDTAVYYCVRGNYVNW GQGTTLTVSS | 13 |
| V1 (CDR grafting) | EVQLVQSGAEVKKPGATVKISCKVSGFNFEDTYIHWVQQAPGKGLEWMGRID PADGDTKHNPKFHDRVTITADTSTDTAYMELSSLRSEDTAVYYCATGNYVNW GQGTTVTVSS | 109 |
| V2 (with back mutations) | EVQLVQSGAEVKKPGATVKISCKASGFNFEDTYIHWVQQAPGKGLEWMGRID PADGDTKHNPKFHDRVTITVDTSTNTAYMELSSLRSEDTAVYYCVRGNYVNW GQGTTVTVSS | 110 |
| V3 (chimeric 2) | QVQLVQSGAEVKKPGASVKVSCKASGFNFEDTYIHWVRQAPGQGLEWMGRID PADGDTKHNPKFHDRVTMTRDTSTSTVYMELSSLRSEDTAVYYCARGNYVNW GQGTTVTVSS | 111 |
| V4 (with back mutations) | QVQLVQSGAEVKKPGASVKVSCKASGFNFEDTYIHWVRQAPGQGLEWMGRID PADGDTKHNPKFHDRVTMTVDTSTNTAYMELSSLRSEDTAVYYCVRGNYVNW GQGTTVTVSS | 112 |

TABLE 8B

| CDR Sequences | | |
|---|---|---|
| CDR | Sequence | SEQ ID NO: |
| CDR-H1 | DTYIH | 103 |
| CDR-H2 | RIDPADGDTKHNPKFHD | 104 |
| CDR-H3 | GNYVM | 105 |

TABLE 7C

| | Humanization of 234B7D5-VL | |
|---|---|---|
| Name | Sequence | SEQ ID NO: |
| 234B7D5 VL | QIVLIQSPAIMSASPGERVTLTCRASSSVTSSYLYWYQQKPGSSPKLWIYSA SNLASGVPARFSGSGSGTSYSLTISSVEAEDAASYFCHQWYSYPRTFGGGTK LEIK | 14 |
| V1 (CDR grafting) | EIVLTQSPATLSLSPGERATLSCRASSSVTSSYLYWYQQKPGQAPRLLIYSA SNLASGIPARFSGSGSGTDFTLTISSLEPEDFAVYYCHQWYSYPRTFGGGTK VEIK | 113 |
| V2 (with back mutations) | EIVLTQSPATLSLSPGERATLSCRASSSVTSSYLYWYQQKPGQAPRLLIYSA SNLASGIPARFSGSGSGTDYTLTISSLEPEDAAVYFCHQWYSYPRTFGGGTK VEIK | 114 |
| V3 (chimeric 2) | EIVLTQSPGTLSLSPGERATLSCRASSSVTSSYLYWYQQKPGQAPRLLIYSA SNLASGIPDRFSGSGSGTDFTLTISRLEPEDFAVYYCHQWYSYPRTFGGGTK VEIK | 115 |
| V4 (with back mutations) | EIVLTQSPGTLSLSPGERATLSCRASSSVTSSYLYWYQQKPGQAPRLLIYSA SNLASGIPDRFSGSGSGTDYTLTISRLEPEDAAVYFCHQWYSYPRTFGGGTK VEIK | 116 |
| V5 (chimeric 3) | EIVMTQSPPTLSLSPGERVTLSCRASSSVTSSYLYWYQQKPGQAPRLLIYSA SNLASGIPARFSGSGSGTDFTLTISSLQPEDFAVYYCHQWYSYPRTFGGGTK VEIK | 117 |
| V6 (with back mutations) | EIVMTQSPPTLSLSPGERVTLSCRASSSVTSSYLYWYQQKPGQAPRLLIYSA SNLASGIPARFSGSGSGTDYTLTISSLQPEDAAVYFCHQWYSYPRTFGGGTK VEIK | 118 |

TABLE 8D

| CDR Sequences | | |
|---|---|---|
| CDR | Sequence | SEQ ID NO: |
| CDR-L1 | RASSSVTSSYLY | 106 |
| CDR-L2 | SASNLAS | 107 |
| CDR-L3 | HQWYSYPRT | 108 |

TABLE 8E

| Humanized antibodies | | | | | | | |
|---|---|---|---|---|---|---|---|
| | VL | VL v1 | VL v2 | VL v3 | VL v4 | VL v5 | VL v6 |
| VH | Chimeric | | | | | | |
| VH v1 | | hz11 | | | | | |
| VH v2 | | | hz22 | | hz24 | | hz26 |
| VH v3 | | | | hz33 | | | |
| VH v4 | | | hz42 | | hz44 | | hz46 |

Example 6. Testing of Humanized Antibodies

This example tested some of the humanized antibodies for the ability to block interactions between SIRPα and CD47.

Recombinant CD47-Fc fusion protein (Acrobiosystems) was coated at 1 µg/ml in PBS onto microtiter plates for 16 hours at 4° C. After blocking for 1 h with 1% BSA in PBST at RT, 1 µg/mL of SIRPα-His protein was added either in the absence or presence of different concentrations of the anti-SIRPα antibodies at RT for 1 h. Plates were subsequently washed three times and incubated with an HRP-conjugated anti-His secondary antibody for 1 h at RT. After washing, the TMB solution was added to each well for 30 min and the reaction was stopped with 2M $H_2SO_4$, and OD was measured at 490 nm.

All of the antibodies listed in Tables 2E (248G3F6), 3E (300A6A6), and 4E (102A10F2) were tested and exhibited high IC50 (Table 9).

TABLE 9

| Activities of humanized antibodies to block SIRPα interaction with CD47 | | |
|---|---|---|
| | Antibody | $IC_{50}$ (nM) |
| 248G3F6 | 02-chi | 0.14 |
| | 02-hz22 | 0.092 |
| | 02-hz32 | 0.11 |
| | 02-hz42 | 0.12 |
| | 02-hz52 | 0.11 |
| 300A6A6 | 03-chi | 0.14 |
| | 03-hz22 | 0.16 |
| | 03-hz32 | 0.145 |
| | 03-hz42 | 0.13 |
| | 03-hz52 | 0.13 |

TABLE 9-continued

Activities of humanized antibodies to block SIRPα interaction with CD47

|  | Antibody | IC$_{50}$ (nM) |
|---|---|---|
| 102A10F2 | 01-hz22 | 0.21 |
|  | 01-hz32 | 0.16 |
|  | 01-hz52 | 0.23 |
|  | 01-hz61 | 0.21 |
|  | 01-hz62 | 0.16 |

Example 7. Increase of Macrophage Mediated Phagocytosis of Tumor Cells

This example tested some of the humanized antibodies for their ability to increase macrophage mediated phagocytosis of tumor cells.

PBMCs were isolated from human blood, and monocytes were differentiated into macrophages using a standard protocol. The monocyte derived macrophages (MDMs) were scraped and re-plated in 24-well dishes and allowed to adhere for 24 hrs. The human tumor cell line Raji that endogenously expressed CD47 were selected as target cells and labeled with 1 uM CFSE for 10 mins, then added to MDMs at a ratio of 5:1 tumor cells per phagocyte and different concentrations of anti-SIRPα antibodies was added at the indicated concentrations. After 3 hr incubation, non-phagocytosed target cells were washed away with PBS and the remaining phagocytes were scraped off, stained with C76 antibody, and analyzed by flow cytometry. Phagocytosis was measured by gating on C76$^+$ cells and then assessing the percentage of CFSE$^+$ cells.

Figure 5:
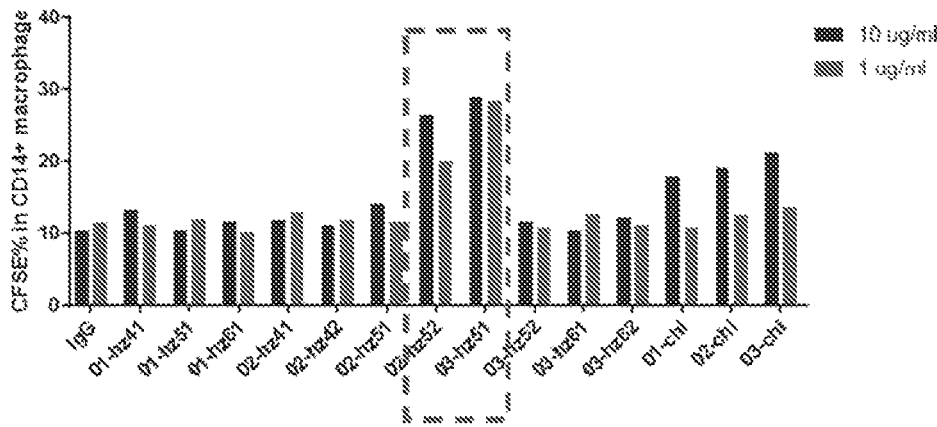
FIG. 5 shows increase of macrophage mediated phagocytosis of tumor cells by the antibody treatments.
Figure 6:
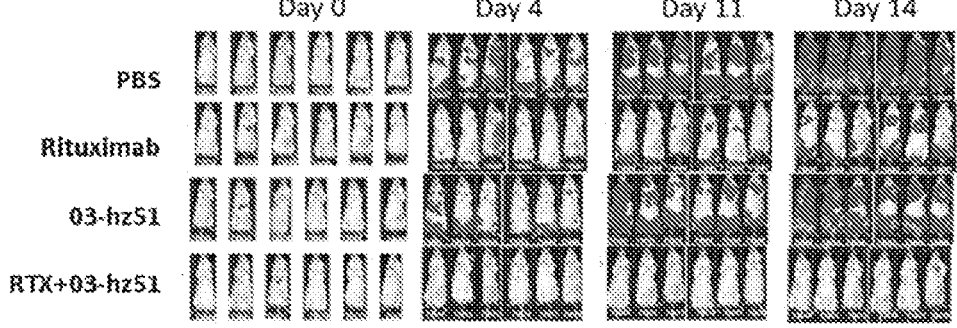
FIG. 6 presents animal scanning images and charts showing that 03-hz51 synergized with rituximab in the complete inhibition of tumor growth in Raji lymphoma tumor model.
Figure 6:
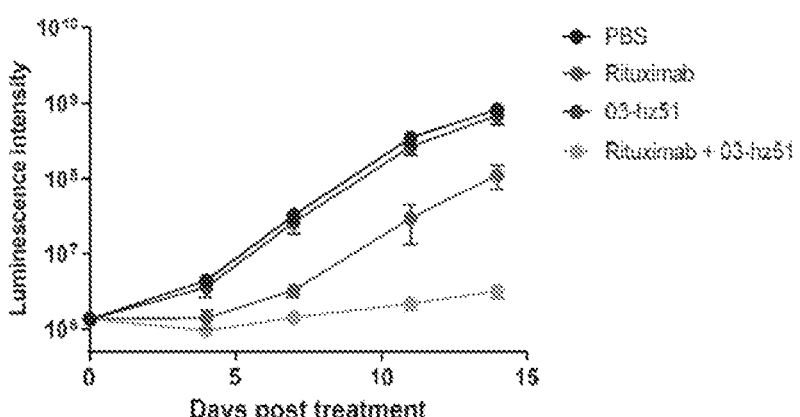

The results are presented in FIG. 5. Out of the tested antibodies, 02-hz52 (248G3F6) and 03-hz51 (300A6A6) exhibited the highest activities, and all others showed excellent activities as well.

Example 8. Binding Affinity to SIRPα v1 and v2

Humanized antibodies 02-hz52 (248G3F6) and 03-hz51 (300A6A6) were tested for their binding affinities to SIRPα v1 and v2 in this example.

The binding kinetics assay of antibody to antigen was performed using Biacore 8K system through human antibody capture approach. The anti-mouse Fc IgG were immobilized on CM5 sensor chip according to the manufactory's instruction. The test antibody was injected and captured by the immobilized anti-human Fc IgG. And then serial concentrations of human SIRPα v1 or SIRPα v2 protein were individually injected, and the binding profile was recorded for each concentration antigen analyte, respectively. The assay system was regenerated by injection of 10 mM Glycine-HCl pH 1.5 for 30 seconds. The running buffer was HBS-EP+ (10 mM HEPES, pH 7.4, 150 mM NaCl, 3 mM EDTA and 0.05% P20). The assay temperature was 25° C., and the association and dissociation time were 180 and 600 seconds, respectively. The Biacore data were fitted using Biacore K8 evaluation software 1.0 according to 1:1 binding model to calculate the association (ka) and dissociation (kd) rate constants as well as the equilibrium constant (KD).

The testing results are shown in Table 10A-B.

TABLE 10A

Binding affinity against SIRPα v1

| Sample | ka (1/Ms) | kd (1/s) | KD (M) |
|---|---|---|---|
| 02-hz52 | 7.04E+05 | 2.98E−04 | 4.23E−10 |
| 03-hz51 | 8.05E+05 | 8.04E−04 | 9.99E−10 |

TABLE 10B

Binding affinity against SIRPα v2

| Sample | ka (1/Ms) | kd (1/s) | KD (M) |
|---|---|---|---|
| 02-hz52 | 3.33E+05 | 2.47E−03 | 7.40E−09 |
| 03-hz51 | 3.31E+05 | 1 00E−03 | 3.03E−09 |

Example 9. Developability Studies

Antibodies 02-hz52 (248G3F6) and 03-hz51 (300A6A6), fused to human IgG4 heavy chain constant regions and kappa light chain constant regions, were tested for their developability. Both antibodies do not contain free cysteines. The testing results showed that both antibodies can be purified to reach clinical grade purities, have suitable Tm, acid/base peak ratios, hydrophobicity, and pI. The results are presented in Table 11.

TABLE 10A

Binding affinity against SIRPα v1

| Sample | Aggregates | SEC (% monomer) | Yield (mg/L) | pI | Acidic peak | Main peak | Basic peak | Tm pH7.5 (° C.) | HIC (NH$_4$)$_2$SO$_4$ (M) |
|---|---|---|---|---|---|---|---|---|---|
| 02-hz52 | Not detected | 99.2 | >10 | 6.9 | 35.5 | 57.2 | 7.2 | 65/71 | 1.02 |
| 03-hz51 | Not detected | 97.91 | >10 | 7.9 | 34.5 | 62.3 | 3.2 | 65/74 | 0.96 |

Example 10. In Vivo Testing

This example tested the efficacy of humanized antibody 03-hz51 (300A6A6) in mice, alone or in combination with rituximab.

Raji-Luc cells resuspended in PBS were inoculated into the tail vein of B-NDG-hSIRPα humanized mice at a concentration of $1 \times 10^5$ cells/0.2 mL and a volume of 0.2 mL/head. A small animal imaging device was used to measure the tumor imaging signal value on the third day of inoculation. When the average imaging signal intensity reached $1.35 \times 10^6$ p/sec, the animals were divided into groups according to the tumor imaging signal value and animal weight, and allocated evenly in 4 experiments There were 6 mice in each experimental group.

Rituximab exhibited a significant inhibitory effect on Raji-Luc lymphoma at a dose level of 10 mg/kg, with no clinically adverse symptoms. 03-hz51 in combination with rituximab (10 mg/kg+0.1 mg/kg) showed a significant inhibitory effect on Raji-Luc lymphoma. The data show that 03-hz51 synergized with rituximab in the complete inhibition of tumor growth in the Raji lymphoma tumor model.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 15, the CDRH2 comprises the amino acid sequence of SEQ ID NO: 16, 21 or 22, the CDRH3 comprises the amino acid sequence of SEQ ID NO: 17, the CDRL1 comprises the amino acid sequence of SEQ ID NO: 18, the CDRL2 comprises the amino acid sequence of SEQ ID NO: 19, and the CDRL3 comprises the amino acid sequence of SEQ ID NO: 20.

2. The antibody or fragment thereof of claim 1, wherein the heavy chain variable region comprises an amino acid sequence selected from the group consisting of SEQ ID NO: 1 and 23-27, or a peptide having at least 90% sequence identity to an amino acid sequence selected from the group consisting of SEQ ID NO: 1 and 23-27.

3. The antibody or fragment thereof of claim 1, wherein the light chain variable region comprises an amino acid sequence selected from the group consisting of SEQ ID NO:2 and 28-29, or a peptide having at least 90% sequence identity to an amino acid sequence selected from the group consisting of SEQ ID NO:2 and 28-29.

4. The antibody or fragment thereof of claim 1, wherein the heavy chain variable region comprises the amino acid sequence of SEQ ID NO:27 and the light chain variable region comprises the amino acid sequence of SEQ ID NO:29.

5. An antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 and a light chain variable region light chain comprising complementarity determining regions CDRL1, CDRL2, and CDRL3, and wherein the CDRH1 comprises the amino acid sequence of SEQ ID NO: 30, the CDRH2 comprises the amino acid sequence of SEQ ID NO: 31, 36, 37 or 38, the CDRH3 comprises the amino acid sequence of SEQ ID NO: 32, the CDRL1 comprises the amino acid sequence of SEQ ID NO: 33, the CDRL2 comprises the amino acid sequence of SEQ ID NO: 34, and the CDRL3 comprises the amino acid sequence of SEQ ID NO: 35.

6. The antibody or fragment thereof of claim 2, wherein the heavy chain variable region comprises an amino acid sequence selected from the group consisting of SEQ ID NO:3 and 39-44, or a peptide having at least 90% sequence identity to an amino acid sequence selected from the group consisting of SEQ ID NO:3 and 39-44.

7. The antibody or fragment thereof of claim 5, wherein the light chain variable region comprises an amino acid sequence selected from the group consisting of SEQ ID NO:4 and 45-46, or a peptide having at least 90% sequence identity to an amino acid sequence selected from the group consisting of SEQ ID NO:4 and 45-46.

8. The antibody or fragment thereof of claim 5, wherein the heavy chain variable region comprises the amino acid sequence of SEQ ID NO:43 and the light chain variable region comprises the amino acid sequence of SEQ ID NO:45.

9. An antibody or fragment thereof having binding specificity to a wild-type human signal regulatory protein alpha (SIRPα) protein, wherein the antibody or fragment thereof comprises a heavy chain variable region comprising heavy chain complementarity determining regions CDRH1, CDRH2, and CDRH3 comprising the amino acid sequences of VH CDR1, VH CDR2, and VH CDR3 of SEQ ID NO: 43 respectively, and a light chain variable region light chain comprising complementarity determining regions CDRL1, CDRL2, and CDRL3 comprising the amino acid sequences of VL CDR1, VL CDR2, and VL CDR3 of SEQ ID NO:45 respectively.

10. The antibody or antigen-binding fragment thereof of claim 9, wherein the VH CDR1, VH CDR2, and VH CDR3 of SEQ ID NO:43 and the VL CDR1, VL CDR2, and VL CDR3 of SEQ ID NO:45 are defined according to the Kabat system.

11. The antibody or antigen-binding fragment thereof of claim 9, wherein the VH CDR1, VH CDR2, and VH CDR3 of SEQ ID NO:43 and the VL CDR1, VL CDR2, and VL CDR3 of SEQ ID NO:45 are defined according to the Chothia system.

12. The antibody or fragment thereof of claim 9, wherein the heavy chain variable region comprises the amino acid sequence of SEQ ID NO:43 and the light chain variable region comprises the amino acid sequence of SEQ ID NO:45.

13. A composition comprising the antibody or fragment thereof of claim 9 and a pharmaceutically acceptable carrier.

* * * * *